(12) United States Patent
Yang et al.

(10) Patent No.: US 12,180,140 B2
(45) Date of Patent: Dec. 31, 2024

(54) COMPOUNDS AND METHODS FOR LIQUID PHASE OLIGONUCLEOTIDE SYNTHESIS

(71) Applicant: Hongene Biotech Corporation, Union City, CA (US)

(72) Inventors: Gaomai Yang, Union City, CA (US); Min Xie, Union City, CA (US); Hongrong Yang, Union City, CA (US); Shengdong Wang, Union City, CA (US); Aldrich N. K. Lau, Palo Alto, CA (US); Ruiming Zou, Union City, CA (US); David Yu, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/390,545

(22) Filed: Dec. 20, 2023

(65) Prior Publication Data

US 2024/0228433 A1    Jul. 11, 2024

Related U.S. Application Data

(60) Provisional application No. 63/477,148, filed on Dec. 23, 2022.

(51) Int. Cl.
| | |
|---|---|
| C07C 237/22 | (2006.01) |
| C07C 231/00 | (2006.01) |
| C07C 233/59 | (2006.01) |
| C07H 1/00 | (2006.01) |
| C07H 21/00 | (2006.01) |

(52) U.S. Cl.
CPC .......... *C07C 237/22* (2013.01); *C07C 231/00* (2013.01); *C07C 233/59* (2013.01); *C07H 1/00* (2013.01); *C07H 21/00* (2013.01)

(58) Field of Classification Search
None
See application file for complete search history.

(56) References Cited

U.S. PATENT DOCUMENTS

| | | |
|---|---|---|
| 5,798,210 A | 8/1998 | Canard et al. |
| 6,677,120 B2 | 1/2004 | Shanghvi et al. |
| 7,276,599 B2 | 10/2007 | Moore et al. |
| 8,143,369 B2 | 3/2012 | Fujiwara et al. |
| 8,450,504 B2 | 5/2013 | Hedrick et al. |
| 8,664,357 B2 | 3/2014 | Livingston |
| 9,029,528 B2 | 5/2015 | Hirai et al. |
| 10,544,456 B2 | 1/2020 | Esfandyarpour et al. |
| 11,725,073 B2 | 8/2023 | Lau et al. |
| 11,851,454 B2 | 12/2023 | Yang et al. |
| 2002/0120096 A1 | 8/2002 | Tsuchida et al. |
| 2002/0123609 A1 | 9/2002 | Frechet et al. |
| 2013/0225789 A1 | 8/2013 | Sun et al. |
| 2013/0231260 A1 | 9/2013 | Lau et al. |
| 2014/0287945 A1 | 9/2014 | Lau et al. |
| 2015/0306034 A1 | 10/2015 | Gao et al. |
| 2018/0023122 A1 | 1/2018 | Crameri et al. |
| 2018/0100190 A1 | 4/2018 | Esfandyarpour et al. |
| 2024/0002420 A1 | 1/2024 | Yang et al. |
| 2024/0092817 A1 | 3/2024 | Yang et al. |

FOREIGN PATENT DOCUMENTS

| | | |
|---|---|---|
| EP | 0 850 949 | 7/1998 |
| EP | 1 710 249 | 1/2005 |
| EP | 2 857 412 | 4/2015 |
| FR | 2623510 | 5/1989 |
| WO | WO 90/06934 | 6/1990 |
| WO | WO 02/079215 | 10/2002 |
| WO | WO 03/093346 | 11/2003 |
| WO | WO 05/123139 | 12/2005 |
| WO | WO 16/160475 | 10/2016 |
| WO | WO 2020/155879 | 8/2020 |

OTHER PUBLICATIONS

Noguchi et al. (J. Chromatography A, 2015, 1392, 56, supplementary data). (Year: 2015).*
Noguchi et al. (J. Chromatography A, 2015, 1392, 56). (Year: 2015).*
Beaucage et al., 1992, Advances in the synthesis of oligonucleotides by the phosphoramidite approach, Tetrahedron, 48(12):2223-2311.
Bonora et al., 1990, HELP (high efficiency liquid phase) new oligonucleotide synthesis on soluble polymeric support, Nucleic Acids Research, 18(11)3155-3159.
Bonora et al., 1993, Large scale, liquid phase synthesis of oligonucleotides by the phosphoramidite approach, Nucleic Acids Research, 21(5):1213-1217.
Carey, 1992, Organic Chemistry, 2d ed., McGraw-Hill, Inc., New York, pp. 328-331.
CAS RN 1242174-86-2, STN Entry Date Sep. 21, 2010 2-amino-N1, N5-dioctadecyl-(2R)-Pentanediamide.
CAS RN 2305302-37-6, STN Entry Date Apr. 24, 2019 2-amino-N1, N5-dihexadecyl-(2R)-Pentanediamide.
CAS RN 2499487-98-6, STN Entry Date Oct. 29, 2020 2-amino-N1, N5-dioctadecyl-Pentanediamide.
CAS RN 752950-25-7, STN Entry Date Sep. 27, 2004 2-amino-N1, N5-dioctadecyl-(2S)-Pentanediamide.
CAS RN 911295-39-1, STN Entry Date Oct. 26, 2006 2-amino-N1, N5-didodecyl-Pentanediamide.
CAS RN 94989-30-7, STN Entry Date Mar. 3, 1985 2-amino-N, N'-dihexadecyl-(2S)-Pentanediamide.

(Continued)

*Primary Examiner* — Sudhakar Katakam
*Assistant Examiner* — Jennifer C Sawyer
(74) *Attorney, Agent, or Firm* — Knobbe, Martens, Olson & Bear, LLP

(57) ABSTRACT

The present disclosure relates to methods and compounds for liquid phase oligonucleotide synthesis employing the use of small molecules with lipophilic groups. Methods for making an oligonucleotide by liquid phase oligonucleotide synthesis using the compounds described herein are also provided.

26 Claims, No Drawings

(56) References Cited

OTHER PUBLICATIONS

Creusen et al., 2020, Scalable one-pot-liquid-phase oligonucleotide synthesis for model network hydrogels, ChemRxiv., preprint. https://doi.org/10.26434/chemrxiv.12327569.v1.
Feng et al., 2001, Synthesis and characterization of new block copolymers with poly(ethylene oxide) and poly[3(S)-sec butylmorphoine-2,5-dione] sequences, Macromol. Biosci., 1:30-39.
Gorelov et al., 1979, Thermal decomposition of poly(phenyl- and poly(pentafluorophenyl acrylates)), Vysokomolekularnye Soedineniya, Seriya B: Bratkie Soobshcheniya, 21(6):410-413 (abstract).
Gravert et al., 1997, Organic synthesis on soluble polymer supports: liquid-phase methodologies, Chem. Rev., 97:489-509.
Greene et al., 1999, Protective Groups in Organic Synthesis, 3rd Ed., John Wiley & Sons, New York (TOC).
Katayama et al., 2018, Liquid-phase synthesis of oligonucleotides, in Synthesis of Therapeutic Oligonucleotides, Obika et al., eds., Springer Nature Singapore Pte Ltd., pp. 83-95.
Kim et al., 2013, Liquid-phase RNA synthesis by using alkyl-chain-soluble support, Chem. Eur. J., 19:8615-8620.
Livingston, Jan. 2, 2020, Liquid phase oligonucleotide synthesis, Oxford Global, Biologics Series, 2 pp.
McMurry, 2000, Organic Chemistry, 5th ed., Brooks/Cole, Pacific Grove, CA, pp. 398 and 408.
McOmie, ed., 1973, Protective Groups in Organic Chemistry, Plenum Press (TOC).
Merrifield, Jul. 20, 1963, Solid phase peptide synthesis. I. The synthesis of a tetrapeptide, J. Am. Chem. Soc., 85(14):2149-2154.
Merrifield, Oct. 8, 1965, Automated synthesis of peptides: solid-phase peptide synthesis, a simple and rapid synthetic method, has now been automates, Science, 150(3693):178-185.

Molina et al., 2019, Liquid-phase oligonucleotide synthesis: past, present, and future predictions, Current Protocols in Nucleic Acid Chemistry, 77:e82, 17 pp.
Scheit, 1980, Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Takahashi et al., 2012, Development of an efficient liquid-phase peptide synthesis protocol using a novel fluorene-derived anchor support compound with Fmoc chemistry; AJIPHASE®, Tetrahedron Lett., 53:1936-1939.
Takahashi et al., 2012, Novel diphenylmethyl-derived amide protecting group for efficient liquid-phase peptide synthesis: AJIPHASE, Organic Lett., 14:4514-4517.
Takahashi et al., 2017, AJIPHASE®: a highly efficient synthetic method for one-pot peptide elongation in the solution phase by an Fmoc strategy, Angew. Chem. Int. Ed., 56:7803-7807.
Uhlman et al., Jun. 1990, Antisense oligonucleotides: a new therapeutic principle, Chemical Reviews, 90(4):543-584.
Wang et al., 2016, Recent advances in regenerated cellulose materials, Progress in Polymer Science, 53:169-206.
Zhang et al., 2015, Tuning multiple arms for camptothecin and folate conjugations on star-shaped copolymers to enhance glutathione-mediated intracellular drug delivery, Polymer Chemistry, 6:2192-2203.
International Search Report and Written Opinion dated Mar. 26, 2024 in international application No. PCT/US2023/085030, filed Dec. 20, 2023.

* cited by examiner

COMPOUNDS AND METHODS FOR LIQUID PHASE OLIGONUCLEOTIDE SYNTHESIS

BACKGROUND

Field

The present disclosure relates to methods and compounds for liquid phase oligonucleotide synthesis employing the use of small molecules with lipophilic groups.

Description of the Related Art

Oligonucleotide-based drugs have become a powerful epitome having ability to treat various diseases. Currently, the demand for oligonucleotides can be fulfilled by conventional solid phase oligonucleotide synthesis (SPOS). There are certain advantages of SPOS, such as simple product isolation and the use of anhydrous synthetic environment. However, the SPOS generally has low overall yield after multiple steps for an oligo sequence and high cost for reagents, solid support and waste management. In addition, SPOS may result in mismatched oligo sequences which leads to difficulty in purification. The increasing demand for metric ton quantities of oligonucleotides far exceeds the production capacity of solid phase oligonucleotide synthesis.

Liquid phase oligonucleotide synthesis (LPOS) is a technology with the potential to provide the production capacity that will be required. One of the major advantages of LPOS over SPOS is the absence of the heterogeneous nature of the process, i.e., insoluble solid supports are not present. The use of a soluble scaffold or support employed in LPOS allows each step of the synthesis to be performed in the liquid phase with improved kinetics.

LPOS utilizing soluble supports having alkyl chains is a strategy that may be employed to synthesize oligonucleotides using homogenous reaction conditions that can facilitate product separation, e.g., via precipitation, and subsequent purification. The hydrophobicity of the soluble support having alkyl chains are also compatible with oligonucleotide synthesis, as anhydrous conditions are often required for oligonucleotide chain elongation using phosphoramidite chemistry. Therefore, further exploration of compounds having long alkyl chains as soluble supports shows great prospects for LPOS development.

SUMMARY

Some aspects of the present disclosure relate to a compound for liquid phase oligonucleotide synthesis having the structure of Formula (I):

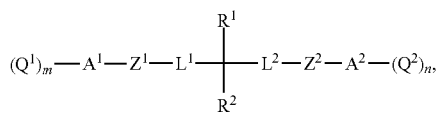

(I)

wherein:
$R^1$ is hydrogen, $C_1$-$C_6$ alkyl, or -$L^3$-$Z^3$-$A^3$-$(Q^3)_p$;
$R^2$ is —$(CH_2)_x NHR^3$, —$(CH_2)_x OR^4$, or —$(CH_2)_x$—C(=O)$R^5$;
$R^3$ is hydrogen or an amino protecting group, or the hydrogen in —$NHR^3$ is absent and $R^3$ is a divalent amino protecting group;
$R^5$ is —$NR^6$—($C_1$-$C_{10}$ alkylene)-$NHR^7$ or —$NR^6$—($C_1$-$C_{10}$ alkylene)-$OR^8$;
$R^6$ is hydrogen or $C_1$-$C_6$ alkyl;
$R^7$ is hydrogen or an amino protecting group, or the hydrogen in —$NHR^7$ is absent and $R^7$ is a divalent amino protecting group;
each of $R^4$ and $R^8$ is independently H or a hydroxy protecting group;
$Z^1$ is —C(=O)$NR^9$—;
$Z^2$ is —C(=O)$NR^{10}$—;
$Z^3$ is —C(=O)$NR^{11}$—;
each of $R^9$, $R^{10}$ and $R^{11}$ is independently hydrogen or $C_1$-$C_6$ alkyl;
each of $L^1$, $L^2$, and $L^3$ is independently a bond, $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, optionally substituted $C_3$-$C_{10}$ cycloalkylene, substituted $C_1$-$C_{20}$ alkylene or substituted 2 to 20 membered heteroalkylene in which one or more methylene repeating units in the substituted $C_1$-$C_{20}$ alkylene or substituted 2 to 20 membered heteroalkylene is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;
each of $A^1$, $A^2$, and $A^3$ is independently $R^A$, —$(CH_2)_y$—($C_6$-$C_{10}$ membered aryl), —$(CH_2)_y$-(5-10 membered heteroaryl), —$(CH_2)_y$—($C_5$-$C_{10}$ cycloalkyl), or —$(CH_2)_y$-(5 to 10 membered heterocyclyl);
each of $Q^1$, $Q^2$ and $Q^3$ is independently —$OR^A$;
each $R^A$ is independently $C_6$-$C_{30}$ alkyl, $C_6$-$C_{30}$ alkenyl, $C_6$-$C_{30}$ alkynyl, 6-30 membered heteroalkylene, —C(=O)($C_6$-$C_{30}$ alkyl), or —C(=O)(6-30 membered heteroalkylene);
each of x and y is independently 0, 1, 2, 3, 4, 5, 6, 7, 8, 9 or 10; and
each of m, n, and p is independently 0, 1, 2, or 3.

In some embodiments, the compound described herein is a compound of Formula (IIa), (IIb), (IIc), (IId), (IIe), or (IIf):

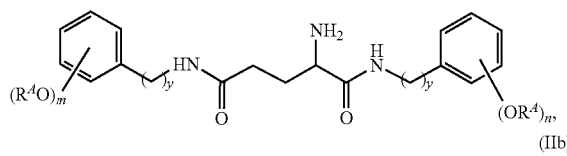

(IIa)

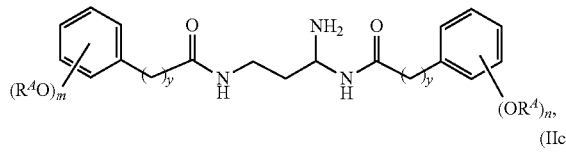

(IIb)

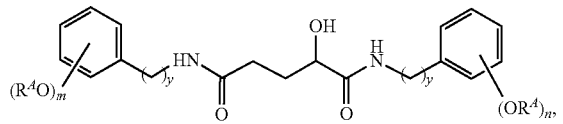

(IIc)

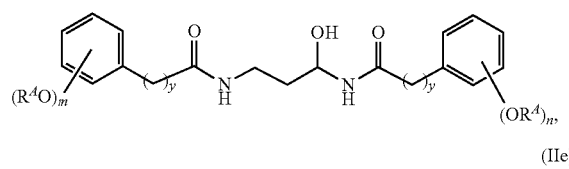
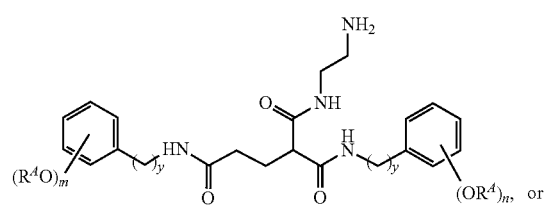
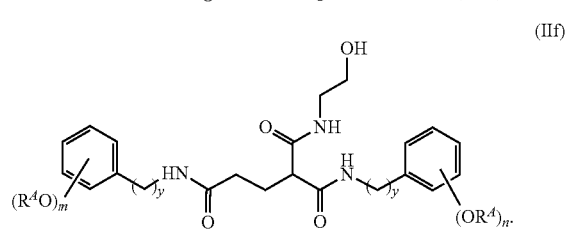
In some embodiments, the compound described herein is a compound of Formula (IIa-1), (IIa-2), (IIa-3), (IIb-1), (IIb-2), (IIc-1), (IIc-2), (IId-1), (IId-2), (IIe-1), (IIe-2), (IIf-1), or (IIf-2):
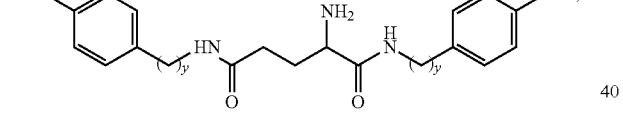
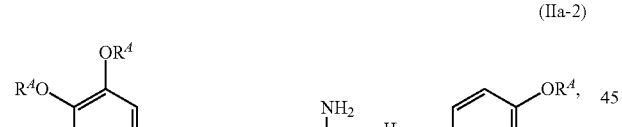
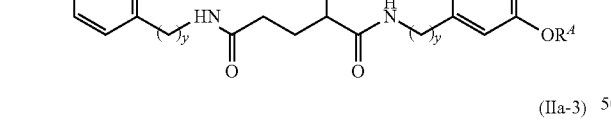
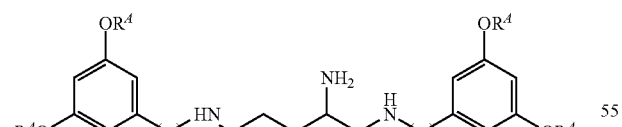
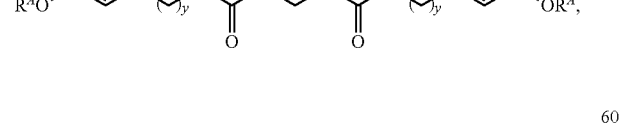
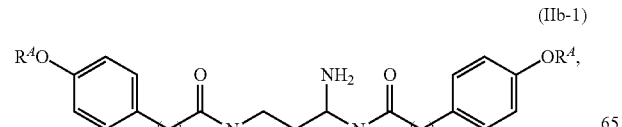
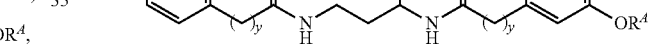

(IIf-2)

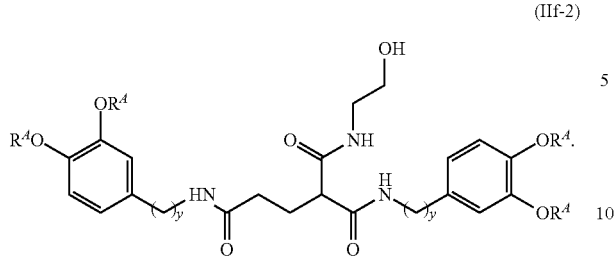

In some embodiments, the compound described herein is a compound of Formula (IIIa), (IIIb), (IIIc), or (IIId):

(IIIa)

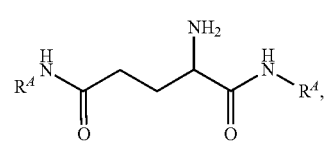

(IIIb)

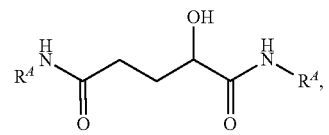

(IIIc)

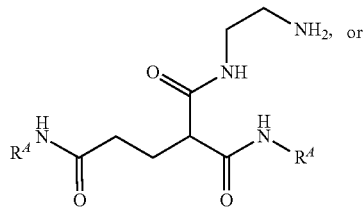

(IIId)

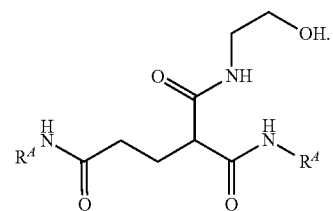

In some embodiments, the compound described herein is a compound having the structure:

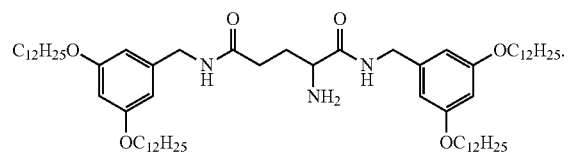

A further aspect of the present disclosure relates to a method for preparing an oligonucleotide by liquid phase oligonucleotide synthesis, comprising:

contacting a compound described herein in a first solvent with one or more nucleoside analogs to form a first solvent solution comprising a first bioconjugate having a structure of Formula (IV):

(IV)

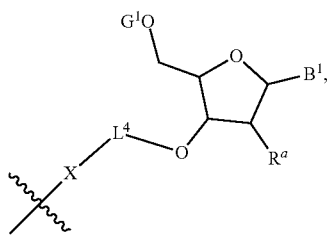

wherein
$B^1$ is a nitrogenous base;
$G^1$ is a 5' hydroxy blocking group;
X is O or $NR^{12}$;
$R^{12}$ is H or $C_1$-$C_6$ alkyl;
$R^a$ is —H, —OH, halogen, —O—($C_1$-$C_6$ alkyl), —O—($C_1$-$C_6$ haloalkyl), or —OY, where Y is a 2' hydroxy protecting group; and
$L^4$ is a cleavable heteroalkylene linker where one or more carbon atoms is replaced by O, S, N, C(=O) or C(=S).

In some embodiments, the method further comprises removing the 5' hydroxy blocking group ($G^1$) to form a 5' unblocked first bioconjugate.

In some embodiments, the method further comprises:
(a) reacting the 5' unblocked first bioconjugate with one or more nucleoside phosphoramidite analogs in a second solvent to form a second bioconjugate comprising the structure of Formula (V):

(V)

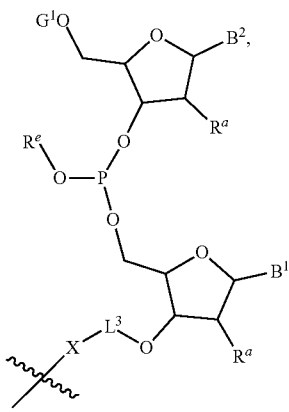

wherein
$G^2$ is a 5' hydroxy blocking group;
$B^2$ is a nitrogenous base; and
$R^e$ is a phosphite protecting group;
(b) oxidizing the phosphite moiety in Formula (V);
(c) removing the 5' blocking group $G^2$ to form a 5' unblocked second bioconjugate comprising the structure of Formula (V'):

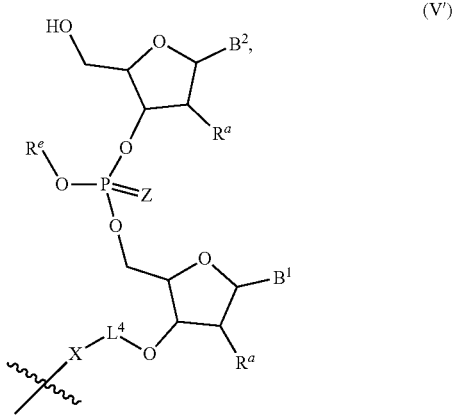

(V')

wherein
Z is O or S; and
(d) isolating or purifying the 5' unblocked second bioconjugate.

A further aspect of the present disclosure relates to an oligonucleotide prepared by the methods described herein.

DETAILED DESCRIPTION

Solid phase oligonucleotide synthesis enable oligo synthesis at the solid support-liquid interface. The solid support is insoluble in the liquid medium (e.g., organic solvent). Examples of solid support include particles of controlled pore glass (CPG) and porous crosslink polystyrene. In contrast, liquid phase oligo synthesis (LPOS) relies on a soluble organic compound as support (hub) to carry out oligo synthesis in solution. Conventional LPOS typically utilizes soluble supports that have one or several functional groups as anchors to conjugate and synthesize oligos. Embodiments of the present disclosure relate to methods for liquid phase oligonucleotide synthesis by using a soluble compound that has a suitable functional group as an anchor for oligo synthesis. For example, the compounds described herein may contain, e.g., a reactive amino group and/or reactive hydroxy group that allows for efficient conjugation with nucleoside or nucleotide analogs with improved yield compared to known liquid phase oligonucleotide synthesis and solid phase oligonucleotide synthesis. The compounds described herein include straight and/or branched aliphatic chains, the selection of which may be used to optimize the solubility of the compound and the growing oligonucleotide chain in organic solvent. The presence of one or more aliphatic chains (such as $C_8$ to $C_{20}$ aliphatic chains) can confer significant hydrophobicity to the small molecule anchor, making it insoluble in polar solvents a characteristic divergent from that of other reactants. This property facilitates an easy separation between the product and impurities, presenting substantial potential to enhance the purity of the final product. The methods described herein is amenable for multi-kilogram oligonucleotide synthesis and good loading capacity and oligo yield.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps but may include additional steps. When used in the context of a compound, composition, or device, the term "comprising" means that the compound, composition, or device includes at least the recited features or components, but may also include additional features or components. By "consisting of" is meant including, and limited to, whatever follows the phrase "consisting of." By "consisting essentially of" is meant including any elements listed after the phrase and limited to other elements that do not interfere with or contribute to the activity or action specified in the disclosure for the listed elements.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

As used herein, common organic abbreviations are defined as follows:
TLC Thin-layer chromatography
NMR Nuclear magnetic resonance
HPLC High-performance liquid chromatography
LC-MS Liquid chromatography-mass spectrometry
DMF Dimethylformamide
DCE 1,2-Dichloroethane
DCM Dichloromethane
CAN Acetonitrile
dT succinate: 5'-O-(4, 4'-dimethoxytrityl)-thymidine-3'-O-succinate, triethylamine salt
HBTU N,N,N',N'-Tetramethyl-O-(1H-benzotriazol-1-yl) uronium hexafluorophosphate HATU 1-[Bis(dimethylamino)methylene]-1H-1,2,3-triazolo[4,5-b]pyridinium 3-oxid hexafluorophosphate
HOBt Hydroxybenzotriazole
DIEA N,N-Diisopropylethylamine
TCA Trichloroacetic acid
TES triethylsilane
ETT 5-(Ethylthio)-1H-tetrazole
mBCPA 3-Chloroperbenzoic acid As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro[3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom, oxygen atom or sulfur atom). For example, a —$CH_2$— may be replaced with —O—, —S—, or —NH—, or a —CH(R)— can be replaced with —N(R)—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$— unit(s). Alternatively and/or additionally, one or more carbon atoms (for example, a —$CH_2$—) can also be substituted with an oxo (=O) to become a carbonyl-C(=O)—, or be substituted with (=S) to become thiocarbonyl —C(=S)—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atoms is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO- and RS-, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N($R_AR_B$)" group in which $R_A$ and $R_B$ can be the same as defined with respect to S-sulfonamido. An O-carbamyl may be substituted or unsubstituted.

An "N-carbamyl" group refers to an "ROC(=O)N($R_A$) -" group in which R and $R_A$ can be the same as defined with respect to N-sulfonamido. An N-carbamyl may be substituted or unsubstituted.

An "O-thiocarbamyl" group refers to a "—OC(=S)—N($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(=S)N($R_A$)—" group in which R and $R_A$ can be the same as defined with respect to N-sulfonamido. An N-thiocarbamyl may be substituted or unsubstituted.

A "C-amido" group refers to a "—C(=O)N($R_AR_B$)" group in which $R_A$ and $R_B$ can be the same as defined with respect to S-sulfonamido. A C-amido may be substituted or unsubstituted.

An "N-amido" group refers to a "RC(=O)N($R_A$)—" group in which R and $R_A$ can be the same as defined with respect to N-sulfonamido. An N-amido may be substituted or unsubstituted.

Where the numbers of substituents are not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

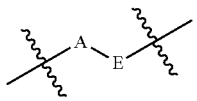

includes the substituent being oriented such that the A is attached at the leftmost attachment point of the molecule as well as the case in which A is attached at the rightmost attachment point of the molecule. In addition, if a group or substituent is depicted as

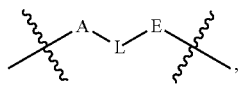

and when L is defined as a bond or absent; such group or substituent is equivalent to

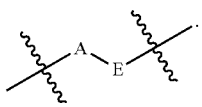

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and compounds described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(═O)CH$_3$ or Ac), or isobutyryl (iBu); arylalkylcarbonyls (e.g., benzyloxycarbonyl or benzoyl (i.e., —C(═O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

Examples of hydroxy protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMTr), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMTr), 9-phenylxanthine-9-yl (Pixyl) and 9-(p-methoxyphenyl)xanthine-9-yl (MOX).

Examples of protecting groups commonly used to protect phosphate and phosphorus hydroxy groups include without limitation, methyl, ethyl, benzyl (Bn), phenyl, isopropyl, tert-butyl, allyl, cyclohexyl (cHex), pivaloyloxymethyl (—$CH_2$—O—C(=O)C($CH_3$)$_3$, or POM), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio)ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino)butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl, 2-cyanoethyl and POM.

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl) amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

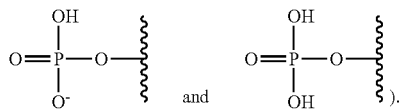 [SMILES: *OP(=O)([O-])O ; *OP(=O)(O)O]

As used herein, the terms "monophosphate," "diphosphate," and "triphosphate" are used in their ordinary sense as understood by those skilled in the art and include protonated forms.

Compounds for Liquid Phase Oligonucleotide Synthesis

Several aspects of the present application relate to a compound for liquid phase synthesis. In some embodiments, the liquid phase synthesis comprises liquid phase oligonucleotide synthesis, liquid phase peptide synthesis, liquid phase polynucleotide (i.e., nucleic acid), synthesis or liquid phase small molecule synthesis. In some embodiments, the compound is a compound for liquid phase oligonucleotide synthesis. The compound may include lipophilic groups, including but not limited to long straight- and branched-chain alkyl, alkenyl, and alkynyl groups, fatty acid esters, or combinations thereof, that allows for improved solubility of the compound and the growing oligonucleotide in organic solvent. The solubility in organic solvent can result in facile purification after addition of each oligonucleotide, allowing for aqueous washes to remove impurities after each coupling step. The length of the PEG arms can be modulated in a manner to reduce trapping of impurities, allowing for improved performance of these structures for liquid phase oligo synthesis.

Compounds of Formula I

Some embodiments of the present disclosure relate to a compound for liquid phase oligonucleotide synthesis, having the structure of Formula (I):

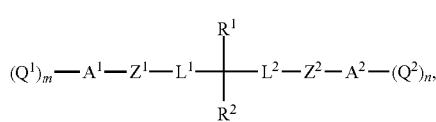

wherein:

$R^1$ is hydrogen, $C_1$-$C_6$ alkyl, or -$L^3$-$Z^3$-$A^3$-$(Q^3)_p$;

$R^2$ is —$(CH_2)_x$NHR$^3$, —$(CH_2)_x$OR$^4$, or —$(CH_2)_x$—C(=O)R$^5$;

$R^3$ is hydrogen or an amino protecting group, or the hydrogen in —NHR$^3$ is absent and $R^3$ is a divalent amino protecting group;

$R^5$ is —NR$^6$—($C_1$-$C_{10}$ alkylene)-NHR$^7$ or —NR$^6$—($C_1$-$C_{10}$ alkylene)-OR$^8$;

$R^6$ is hydrogen or $C_1$-$C_6$ alkyl;

$R^7$ is hydrogen or an amino protecting group, or the hydrogen in —NHR$^7$ is absent and $R^7$ is a divalent amino protecting group;

each of $R^4$ and $R^8$ is independently H or a hydroxy protecting group;

$Z^1$ is —C(=O)NR$^9$—;

$Z^2$ is —C(=O)NR$^{10}$—;

$Z^3$ is —C(=O)NR$^{11}$—;

each of $R^9$, $R^{10}$ and $R^{11}$ is independently hydrogen or $C_1$-$C_6$ alkyl;

each of $L^1$, $L^2$, and $L^3$ is independently a bond, $C_1$-$C_{20}$ alkylene, 2 to 20 membered heteroalkylene, optionally substituted phenylene, optionally substituted 5 to 6 membered heteroarylene, optionally substituted 3 to 10 membered heterocyclylene, optionally substituted $C_3$-$C_{10}$ cycloalkylene, substituted $C_1$-$C_{20}$ alkylene or substituted 2 to 20 membered heteroalkylene in which one or more methylene repeating units in the substituted $C_1$-$C_{20}$ alkylene or substituted 2 to 20 membered heteroalkylene is each independently replaced by a group selected from the group consisting of optionally substituted phenylene, optionally substituted 5 to 6 membered heteroarylene, optionally substituted 3 to 10 membered heterocyclylene, optionally substituted $C_3$-$C_{10}$ cycloalkylene, —C(=O)—, —CH=CH—, and —C≡C—;

each of $A^1$, $A^2$, and $A^3$ is independently $R^A$, —$(CH_2)_y$—($C_6$-$C_{10}$ membered aryl), —$(CH_2)_y$-(5-10 membered heteroaryl), —$(CH_2)_y$—($C_5$-$C_{10}$ cycloalkyl), or —$(CH_2)_y$-(5 to 10 membered heterocyclyl);

each of $Q^1$, $Q^2$ and $Q^3$ is independently —OR$^A$;

each $R^A$ is independently $C_6$-$C_{30}$ alkyl, $C_6$-$C_{30}$ alkenyl, $C_6$-$C_{30}$ alkynyl, 6-30 membered heteroalkylene, —C(=O)($C_6$-$C_{30}$ alkyl), or —C(=O)(6-30 membered heteroalkylene);

each of x and y is independently 0, 1, 2, 3, 4, 5, 6, 7, 8, 9 or 10; and each of m, n, and p is independently 0, 1, 2, or 3.

In some embodiments of the compound of Formula (I), $R^1$ is hydrogen. In other embodiments, $R^1$ is $C_1$-$C_6$ alkyl. In yet other embodiments, $R^1$ is -$L^3$-$Z^3$-$A^3$-$(Q^3)_p$.

In some embodiments of the compound of Formula (I), $R^2$ is —CH(CH$_2$)$_x$NHR$^3$. In some such embodiments, $R^3$ is hydrogen. In other such embodiments, $R^3$ is an amino protecting group, or the hydrogen in —NHR$^3$ is absent and $R^3$ is a divalent amino protecting group. In some embodiments, x is 0. In other embodiments, x is 1. In yet other embodiments, x is 2. In still yet other embodiments, x is an integer greater than 2. For example, in some embodiments, x is 3, 4, 5, 6, 7, 8, 9, or 10.

In other embodiments of the compound of Formula (I), $R^2$ is —CH(CH$_2$)$_x$OR$^4$. In some such embodiments, $R^4$ is H. In other such embodiments, $R^4$ is a hydroxy protecting group. In some embodiments, x is 0. In other embodiments, x is 1. In yet other embodiments, x is 2. In still yet other embodiments, x is an integer greater than 2. For example, in some embodiments, x is 3, 4, 5, 6, 7, 8, 9, or 10.

In yet other embodiments of the compound of Formula (I), $R^2$ is —$(CH_2)_x$—C(=O)$R^5$. In some embodiments, x is 0. In other embodiments, x is 1. In yet other embodiments, x is 2. In still yet other embodiments, x is an integer greater than 2. For example, in some embodiments, x is 3, 4, 5, 6, 7, 8, 9, or 10. In some embodiments, $R^5$ is —$NR^6$—($C_1$-$C_{10}$ alkylene)-$NHR^7$, wherein $R^7$ is hydrogen or an amino protecting group, or the hydrogen in —$NHR^7$ is absent and $R^7$ is a divalent amino protecting group. In other embodiments, $R^5$ is —$NR^6$—($C_1$-$C_{10}$ alkylene)-$OR^8$, wherein $R^8$ is H or a hydroxy protecting group. In some embodiments, $R^5$ is —$NHCH_2CH_2NH_2$. In other embodiments, $R^5$ is —$NHCH_2CH_2OH$.

In some embodiments of the compound of Formula (I), $L^1$ is $C_1$-$C_{20}$ alkylene. In some embodiments, $L^1$ is methylene (—$CH_2$—), ethylene (—$CH_2CH_2$—), propylene (—$CH_2CH_2CH_2$—), butylene (—$CH_2CH_2CH_2CH_2$—), or pentylene (—$CH_2CH_2CH_2CH_2CH_2$—). In some embodiments of the compound of Formula (I), $L^1$ is optionally substituted alkylene. In other embodiments of the compound of Formula (I), $L^1$ is 2 to 20 membered heteroalkylene. In yet other embodiments of the compound of Formula (I), $L^1$ is a bond.

In some embodiments of the compound of Formula (I), $L^2$ is $C_1$-$C_{20}$ alkylene. In some embodiments, $L^2$ is methylene (—$CH_2$—), ethylene (—$CH_2CH_2$—), propylene (—$CH_2CH_2CH_2$—), butylene (—$CH_2CH_2CH_2CH_2$—), or pentylene (—$CH_2CH_2CH_2CH_2CH_2$—). In some embodiments, $L^2$ can be optionally substituted alkylene. In other embodiments of the compound of Formula (I), $L^2$ is 2 to 20 membered heteroalkylene. In yet other embodiments of the compound of Formula (I), $L^2$ is a bond.

In some embodiments of the compound of Formula (I), $L^1$ is $C_1$-$C_{20}$ alkylene and $L^2$ is $C_1$-$C_{20}$ alkylene. In other embodiments of the compound of Formula (I), $L^1$ is $C_1$-$C_{20}$ alkylene and $L^2$ is a bond. In some embodiments of the compound of Formula (I), $L^1$ is a bond and $L^2$ is $C_1$-$C_{20}$alkylene. In some such embodiments, $L^2$ is ethylene.

In some embodiments of the compound of Formula (I), $Z^1$ is —C(=O)NH—, wherein the nitrogen atom is directly bound to $A^1$. In other embodiments, $Z^1$ is —C(=O)NH—, wherein the carbon atom is directly bound to $A^1$.

In some embodiments of the compound of Formula (I), $Z^2$ is —C(=O)NH—, wherein the nitrogen atom is directly bound to $A^2$. In other embodiments, $Z^2$ is —C(=O)NH—, wherein the carbon atom is directly bound to $A^2$.

In some embodiments of the compound of Formula (I), $Z^1$ is —C(=O)NH—, wherein the nitrogen atom is directly bound to $A^1$, and $Z^2$ is —C(=O)NH—, wherein the nitrogen atom is directly bound to $A^2$. In other embodiments of the compound of Formula (I), $Z^1$ is —C(=O)NH—, wherein the carbon atom is directly bound to $A^1$, and $Z^2$ is —C(=O)NH—, wherein the carbon atom is directly bound to $A^2$.

In some embodiments of the compound of Formula (I), $A^1$ is $R^A$. In other embodiments, $A^1$ is $C_6$-$C_{10}$ membered aryl. In some such embodiments, $A^1$ is phenyl. In yet other embodiments of Formula (I), $A^1$ is 5-10 membered heteroaryl. In some such embodiments, $A^1$ is pyridinyl, pyrazinyl, furanyl, or thiophenyl. In some embodiments of the compound of Formula (I), $A^1$ is $C_5$-$C_{10}$ cycloalkyl. In some such embodiments, $A^1$ is cyclopentyl, cyclohexyl, cycloheptyl, or adamantyl. In some embodiments of the compound of Formula (I), $A^1$ is 5 to 10 membered heterocyclyl. In some such embodiments, $A^1$ is piperidinyl, piperazinyl, morpholinyl, or pyranyl.

In some embodiments of the compound of Formula (I), $A^1$ is —$(CH_2)_y$—($C_6$-$C_{10}$ membered aryl). In some such embodiments, $A^1$ is —$CH_2$-phenyl (i.e., benzyl). In yet other embodiments of Formula (I), $A^1$ is —$(CH_2)_y$-(5-10 membered heteroaryl). In some such embodiments, $A^1$ is —$CH_2$-pyridinyl, —$CH_2$-pyrazinyl, —$CH_2$-furanyl, or —$CH_2$-thiophenyl.

In some embodiments of the compound of Formula (I), $A^2$ is $R^A$. In other embodiments, $A^2$ is $C_6$-$C_{10}$ membered aryl. In some such embodiments, $A^2$ is phenyl. In yet other embodiments, of Formula (I), $A^2$ is 5-10 membered heteroaryl. In some such embodiments, $A^2$ is pyridinyl, pyrazinyl, furanyl, or thiophenyl. In some embodiments of the compound of Formula (I), $A^2$ is $C_5$-$C_{10}$ cycloalkyl. In some such embodiments, $A^2$ is cyclopentyl, cyclohexyl, cycloheptyl, or adamantyl. In some embodiments of the compound of Formula (I), $A^2$ is 5 to 10 membered heterocyclyl. In some such embodiments, $A^2$ is piperidinyl, piperazinyl, morpholinyl, or pyranyl.

In some embodiments of the compound of Formula (I), $A^2$ is —$(CH_2)_y$—($C_6$-$C_{10}$ membered aryl). In some such embodiments, $A^2$ is —$CH_2$-phenyl (i.e., benzyl). In yet other embodiments of Formula (I), $A^2$ is —$(CH_2)_y$-(5-10 membered heteroaryl). In some such embodiments, $A^2$ is —$CH_2$-pyridinyl, —$CH_2$-pyrazinyl, —$CH_2$-furanyl, or —$CH_2$-thiophenyl.

In some embodiments of the compound of Formula (I), $A^1$ and $A^2$ are each phenyl. In other embodiments, $A^1$ and $A^2$ are each pyridinyl. In yet other embodiments, $A^1$ and $A^2$ are each benzyl. In still yet other embodiments, $A^1$ and $A^2$ are each —$CH_2$-pyridinyl.

In some embodiments of the compound of Formula (I) wherein $R^1$ is -$L^3$-$Z^3$-$A^3$-$(Q^3)_p$, $L^3$ is $C_1$-$C_{20}$ alkylene. In some such embodiments, $L^3$ is methylene (—$CH_2$—), ethylene (—$CH_2CH_2$—), propylene (—$CH_2CH_2CH_2$—), butylene (—$CH_2CH_2CH_2CH_2$—), or pentylene (—$CH_2CH_2CH_2CH_2CH_2$—). In some embodiments, $L^3$ can be optionally substituted alkylene. In other embodiments of the compound of Formula (I), $L^3$ is 2 to 20 membered heteroalkylene. In yet other embodiments of the compound of Formula (I), $L^3$ is a bond.

In some embodiments of the compound of Formula (I) wherein $R^1$ is -$L^3$-$Z^3$-$A^3$-$(Q^3)_p$, $Z^3$ is —C(=O)NH—, wherein the nitrogen atom is directly bound to $A^3$. In other embodiments, $Z^3$ is —C(=O)NH—, wherein the carbon atom is directly bound to $A^3$.

In some embodiments of the compound of Formula (I) wherein $R^1$ is -$L^3$-$Z^3$-$A^3$-$(Q^3)_p$, $A^3$ is $R^A$. In other embodiments, $A^3$ is $C_6$-$C_{10}$ membered aryl. In some such embodiments, $A^3$ is phenyl. In yet other embodiments, of Formula (I) wherein $R^1$ is -$L^3$-$Z^3$-$A^3$-$(Q^3)_p$, $A^3$ is 5-10 membered heteroaryl. In some such embodiments, $A^3$ is pyridinyl, pyrazinyl, furanyl, or thiophenyl. In some embodiments of the compound of Formula (I) wherein $R^1$ is -$L^3$-$Z^3$-$A^3$-$(Q^3)_p$, $A^3$ is $C_5$-$C_{10}$ cycloalkyl. In some such embodiments, $A^3$ is cyclopentyl, cyclohexyl, cycloheptyl, or adamantyl. In some embodiments of the compound of Formula (I) wherein $R^1$ is -$L^3$-$Z^3$-$A^3$-$(Q^3)_p$, $A^3$ is 5 to 10 membered heterocyclyl. In some such embodiments, $A^3$ is piperidinyl, piperazinyl, morpholinyl, or pyranyl.

In some embodiments of the compound of Formula (I) wherein $R^1$ is -$L^3$-$Z^3$-$A^3$-$(Q^3)_p$, $A^3$ is —$(CH_2)_y$—($C_6$-$C_{10}$ membered aryl). In some such embodiments, $A^3$ is —$CH_2$-phenyl (i.e., benzyl). In yet other embodiments of Formula (I) wherein $R^1$ is -$L^3$-$Z^3$-$A^3$-$(Q^3)_p$, $A^3$ is —$(CH_2)_y$-(5-10 membered heteroaryl). In some such embodiments, $A^3$ is —$CH_2$-pyridinyl, —$CH_2$-pyrazinyl, —$CH_2$— furanyl, or —$CH_2$-thiophenyl.

In some embodiments, the compound described herein may also be represented by structure of Formula (IIa), (IIb), (IIc), (IId), (IIe), or (IIf):

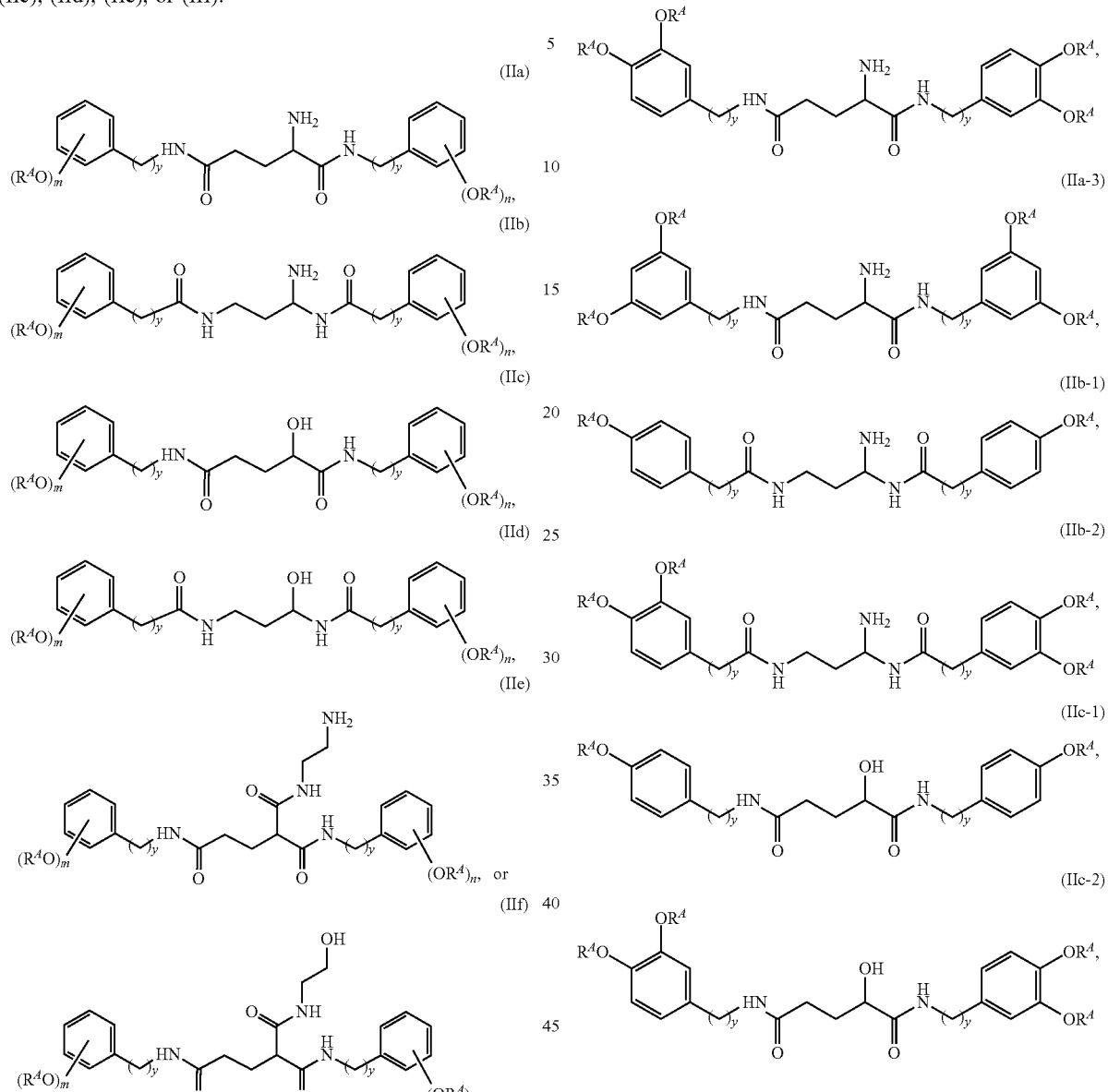

In some embodiments of the compounds of Formula (IIa), (IIb), (IIc), (IId), (IIe), or (IIf), y is 0. In other embodiments, y is 1.

In some further embodiments, the compound described herein may also be represented by structure of Formula (IIa-1), (IIa-2), (IIa-3), (IIb-1), (IIb-2), (IIc-1), (IIc-2), (IId-1), (IId-2), (IIe-1), (IIe-2), (IIf-1), or (IIf-2):

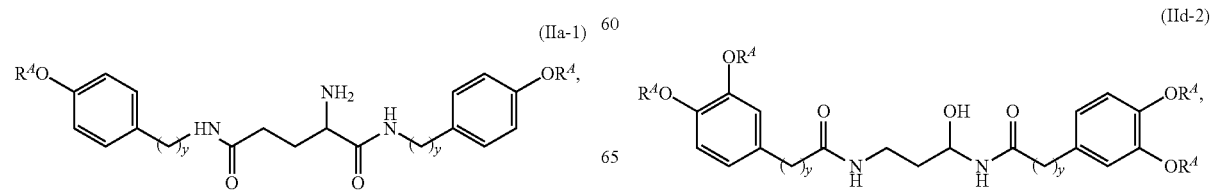

(IIe-1)

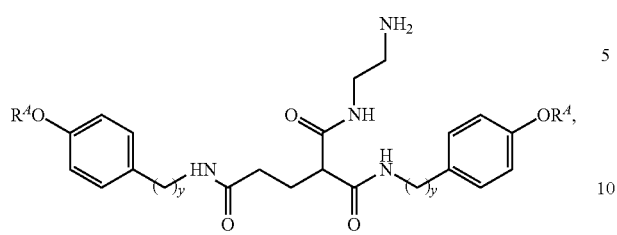

(IIe-2)

(IIf-1)

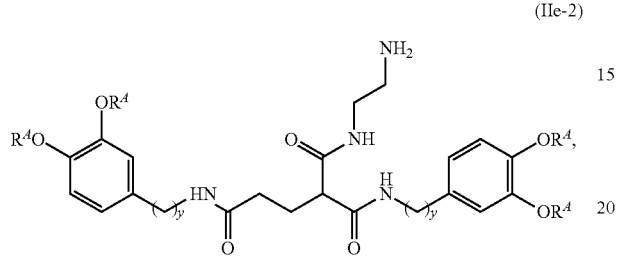

(IIf-2)

In some embodiments of the compounds of Formula (IIa-1), (IIa-2), (IIa-3), (IIb-1), (IIb-2), (IIc-1), (IIc-2), (IId-1), (IId-2), (IIe-1), (IIe-2), (IIf-1), or (IIf-2), y is 0. In other embodiments, y is 1.

In some further embodiments, the compound described herein may also be represented by structure of Formula (IIIa), (IIIb), (IIIc), or (IIId):

(IIIa)

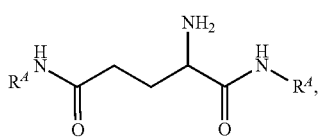

(IIIb)

(IIIc)

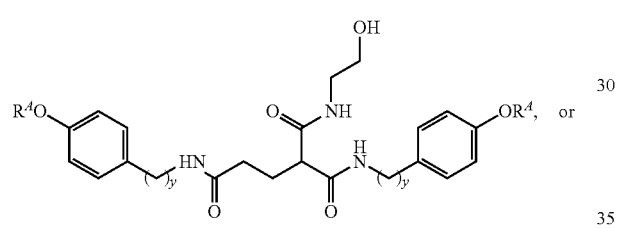

(IIId)

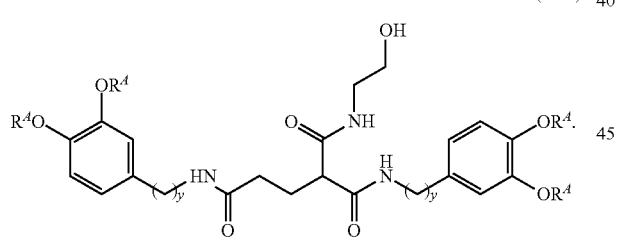

In some embodiments of the compound of Formula (I), (IIa), (IIb), (IIe), (IId), (IIe), (IIf), (IIa-1), (IIa-2), (IIa-3), (IIb-1), (IIb-2), (IIc-1), (IIc-2), (IId-1), (IId-2), (IIe-1), (IIe-2), (IIf-1), (IIf-2), (IIIa), (IIIb), (IIIc), or (IIId), each $R^A$ is independently $C_6$-$C_{30}$ alkyl, $C_1$-$C_{20}$ alkyl or $C_{1-2}$-$C_{18}$ alkyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkyl). In some such embodiments, each $R^A$ is ethylhexyl, dodecyl, 3,5,5-trimethylhexyl, 3,7,11-trimethyldodecyl, In some other embodiments, each $R^A$ is independently $C_6$-$C_{30}$ alkenyl, $C_1$-$C_{20}$ alkenyl or $C_{12}$-$C_{18}$ alkenyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkenyl). In other embodiments, each $R^A$ is independently —C(=O)($C_6$-$C_{30}$ alkyl), —C(=O)($C_{10}$-$C_{30}$ alkyl) or —C(=O)($C_{12}$-$C_{18}$ alkyl). In some such embodiments, each $R^A$ is

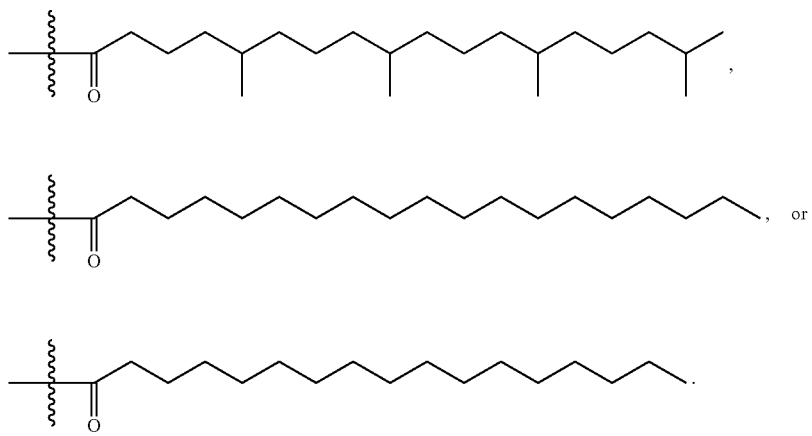

In some embodiments, the compound is

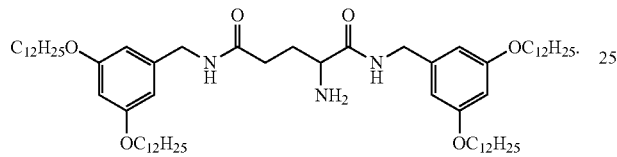

Method of Preparing Oligonucleotide by Liquid Phase Oligonucleotide Synthesis (LPOS)

Another aspect of the present application relates to a method for making a compound by liquid phase synthesis. The compound may be an oligonucleotide, a peptide, a polynucleotide (i.e., nucleic acid), or a small molecule. In certain embodiments, the method is for making an oligonucleotide by liquid phase oligonucleotide synthesis.

In some embodiments of the method described herein, the method includes dissolving a compound as described herein in a first solvent to form a reaction matrix, contacting, or otherwise reacting, the compound with one or more nucleoside analogs to form a first bioconjugate comprising a structure of Formula (IV):

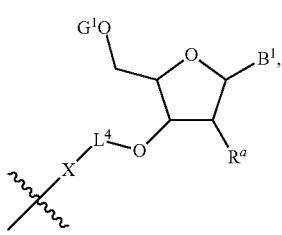

(IV)

wherein $B^1$ is a nitrogenous base; $G^1$ is a 5' hydroxy blocking group; X is O or $NR^{12}$; $R^a$ is —H, —OH, halogen, —O—($C_1$-$C_6$ alkyl), —O—($C_1$-$C_6$ haloalkyl), or —OY, where Y is a 2' hydroxy protecting group; and $L^4$ is a cleavable heteroalkylene linker where one or more carbon atoms is replaced by O, S, N, C(=O) or C(=S). The squiggle line in the structure of Formula (IV) refers to the point of attachment of the first bioconjugate to the small molecular anchor compound described herein. In some such embodiments, the nitrogenous base comprises a purine base, a deazapurine base, or a pyrimidine base. In some embodiments, the structure of Formula (IV) is also represented by Formula (IVa):

(IVa)

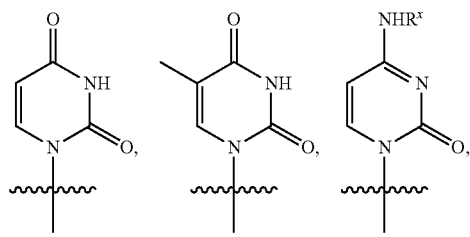

In some embodiments, X is O. In other embodiments, X is $NR^{12}$, and $R^{12}$ is H. In some embodiments, the amide bond —$NR^{12}$—C(=O)— may be formed from the terminal amino group of the compound reacting with a first nucleoside analog containing a 3'succinate (which contains a free carboxy group). In other embodiments, the amide bond —$NR^{12}$—C(=O)— may be formed from a linker bound to the 3' position of the first nucleoside analog. In some embodiments, the ester bond —O—C(=O)— may be formed from the terminal alcohol group of the compound reacting with a first nucleoside analog containing a 3'succinate (which contains a free carboxy group). Other alternative linker may include hydroquinone-O,O'-diacetic acid (HQDA or Q-linker).

In some embodiments of the method described herein, $B^1$ is independently optionally protected adenine, optionally protected deaza adenine, optionally protected cytosine, optionally protected guanine, optionally protected deaza guanine, optionally protected thymine or optionally protected uracil. In some embodiments, $B^1$ is

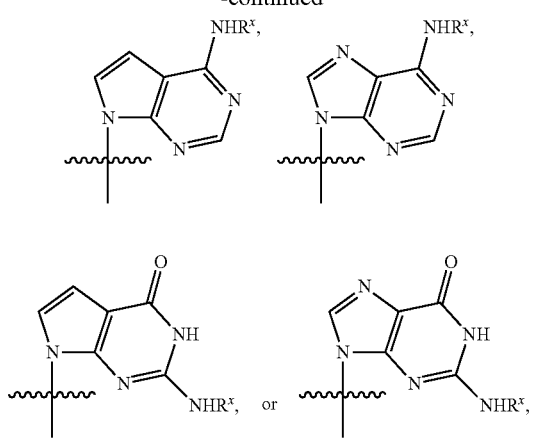

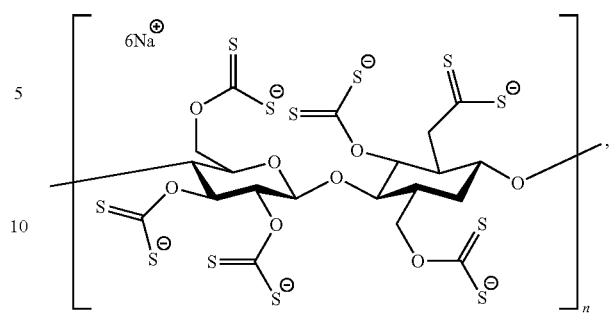

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments, $G^1$ is a trityl type of hydroxy protecting group selected from the group consisting of (4-methoxyphenyl)diphenylmethyl, bis(4-methoxyphenyl) phenylmethyl, tris(4-methoxyphenyl)methyl, 9-phenylxanthen-9-yl, and 9-(4-methoxyphenyl)xanthen-9-yl. In some embodiments, $G^1$ is bis(4-methoxyphenyl)phenylmethyl (DMTr).

In some embodiments of the method described herein, the method further comprises: removing the 5' hydroxy blocking group ($G^1$) to form a 5' unblocked first bioconjugate. In some embodiments, the method may further comprise washing the first solvent solution with an aqueous solvent or solution to remove impurities from 5' unblocked first bioconjugate. In other embodiments, the method may further comprise isolating the 5' unblocked first bioconjugate. In some such embodiments, the isolation of the 5' unblocked first bioconjugate is achieved by precipitation, dialysis or filtration.

In some specific embodiments, the isolation of the 5' unblocked first bioconjugate is achieved by precipitation. In some embodiments, the precipitation of the 5' unblocked first bioconjugate is done by adding the solution comprising the bioconjugate to a solvent comprising pentane, hexane, heptane, dialkyl ethers (e.g., diethyl ether, t-butyl methyl ether, etc.), toluene, isopropyl acetate, dichloromethane, dimethyl sulfoxide, ethyl acetate, alkanols (e.g., methanol, ethanol, isopropanol), or alkenols, or a combination thereof. In some such embodiments, the solvent is diethyl ether. In other such embodiments, the solvent is isopropanol. In other embodiments, the isolation is achieved by a filtration step. The filtration step may include dialysis, filtration, nanofiltration, ultrafiltration, or any known filtration technology suitable for use herein, and combinations thereof. In some embodiments, the filtration step comprises dialysis or filtration. In further embodiments, filtration step includes the use of a membrane. The membrane may comprise a cellulose acetate, a glass fiber, a carbon-based polymer, a regenerated cellulose and combinations thereof. In certain embodiments, the regenerated cellulose has an electrostatic charge. In some embodiments, the regenerated cellulose membrane is negatively charged. In some embodiments, the regenerated cellulose comprises the structure:

In some embodiments, the regenerated cellulose has a molecular weight cutoff (MWCO) from about 5 kDa to about 50 kDa, from about 6 kDa to about 40 kDa, about 7 kDa to about 30 kDa, or about 8 kDa to about 12 kDa. The regenerated cellulose membrane is capable of retaining the PVH containing bioconjugate as an alternative to the expensive nanofiltration membranes prepared with polyimide. The negatively charged membrane capable of reducing nonspecific adsorption of negatively charged biomolecules. In some embodiments, the regenerated cellulose is treated in a process including carbon disulfide followed by an aqueous metal hydroxide. In some embodiments, the regenerated cellulose comprises dithiolate groups and metal cations. In some embodiments, the metal cations comprise group 1 metals (i.e., group IA metals or alkali metals), group 2 metals (i.e., group IIA metals or alkaline earth metals) and combinations thereof. In some embodiments, the metal cations comprise sodium cations.

In some embodiments of the method described herein, the method further comprises: (a) reacting the 5' unblocked first bioconjugate with one or more nucleoside phosphoramidite analogs in a second solvent to form a second bioconjugate comprising the structure of Formula (V):

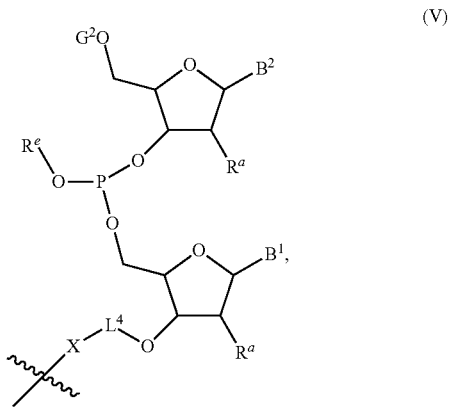

(V)

wherein $G^2$ is a 5' hydroxy blocking group; $B^2$ is a nitrogenous base; and $R^e$ is a phosphite protecting group;

(b) oxidizing the phosphite moiety in Formula (V);

(c) removing the 5' blocking group $G^2$ to form a 5' unblocked second bioconjugate comprising the structure of Formula (V'):

(V')

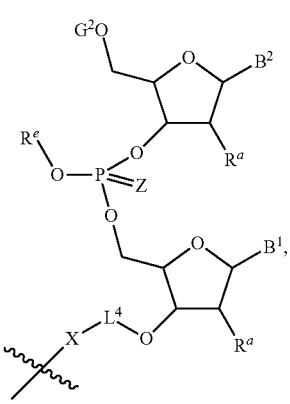

wherein Z is O or S; and (d) purifying or isolating the 5' unblocked second bioconjugate. In some such embodiments, the structure of Formula (V) is also represented by (Va) and the Formula (V') is also represented by Formula (V'a):

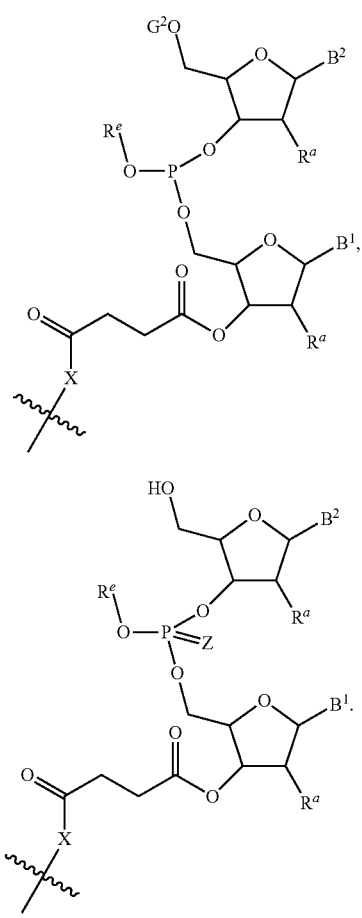

In some such embodiments, $R^e$ is unsubstituted $C_1$-$C_6$ alkyl or substituted $C_1$-$C_6$ alkyl. A nonlimiting example of a substituted $C_1$-$C_6$ alkyl suitable for use as $R^e$ includes —$CH_2CH_2CN$. In some embodiments, the method further comprises blocking unreacted 5' hydroxy group in the 5' unblocked first bioconjugate prior to step (b). In some such embodiments, X is $NR^{12}$, and $R^{12}$ is H. In other such embodiments, X is O.

In some embodiments of the method described herein, $B^2$ is independently optionally protected adenine, optionally protected deaza adenine, optionally protected cytosine, optionally protected guanine, optionally protected deaza guanine, optionally protected thymine, or optionally protected uracil. In some embodiments, $B^2$ is

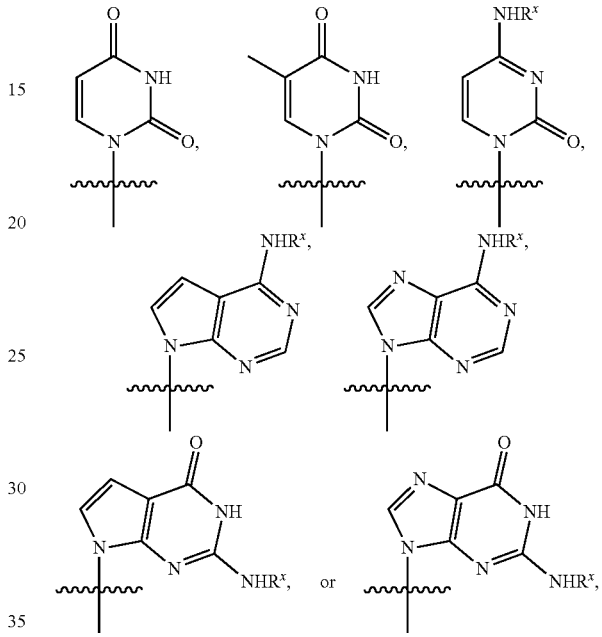

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments of the method described herein, $G^2$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl, and 9-(4-methoxyphenyl)xanthen-9-yl. In some embodiments, $G^2$ is bis(4-methoxyphenyl)phenylmethyl (DMTr).

In some embodiments of the method described herein, the method further comprises blocking unreacted 5' hydroxy group in the 5' unblocked first bioconjugate prior to step (b). In some such embodiment, said blocking is performed by reacting the 5' hydroxy group with acetic anhydride ($Ac_2O$).

In some embodiments, the removal of the 5' blocking group may be accomplished by treatment with an acidic solution. Non-limiting examples of acids that may be used for the acidic solution include trichloroacetic acid, dichloroacetic acid, monochloroacetic acid, and trifluoroacetic acid.

In some embodiments of the method described herein, steps (a)-(d) are repeated multiple cycles until one or more desired length of oligonucleotides have been synthesized. In some such embodiments, steps (a)-(d) are repeated at least about 2, 3, 4, 5, 6, 7, 8, 9, 10, 11, 12, 13, 14, 15, 16, 17, 18, 19 or 20 cycles. In some such embodiments, the oligonucleotide synthesized may comprises at least 2,3,4,5, 6, 7, 8, 9, 10, 11, 12, 13, 14, 15, 16, 17, 18, 19 or 20 bases.

In some embodiments of the method described herein, the purification in step (d) can be achieved by washing the second solvent containing the 5' unblocked second bioconjugate with an aqueous solvent or solution to remove impurities from 5' unblocked second bioconjugate. In other embodiments, the method may further comprise isolating the 5' unblocked second bioconjugate. In some such embodiments, the isolation of the 5' unblocked second bioconjugate is achieved by precipitation, dialysis or filtration, similar to those described herein with respect to the 5' unblocked first bioconjugate.

In some embodiments of the method described herein, the method further comprises removing the oligonucleotides from the compound. In some such embodiments, the removing step includes a step of covalent chemical bond scission. In some embodiments, the removing step includes hydrolysis. In certain embodiments, the removing includes hydrolysis at a temperature from about 0° C. to about 80° C., or about 10° C. to about 60° C., or about 15° C. to about 30° C. In further embodiments, when the first nucleoside is covalently attached to the compound through reaction of the 3'-succinic acid reacting with the amino or alcohol group of the compound, the amide or ester bond formed between the first nucleoside and the compound may be cleaved by hydrolysis.

In some embodiments of the method described herein, each of the first solvent and the second solvent comprise one or more polar solvents or one or more non-polar solvents, or combinations thereof. In some embodiments, the one or more non-polar solvents comprises diethyl ether, cyclopentyl methyl ether (CPME), methyl t-butyl ether (MTBE), ethyl acetate (EtOAc), toluene, hexane, pentane, heptane, dichloromethane (DCM), chloroform, or combinations thereof. In some embodiments, the one or more polar solvents comprises acetonitrile, tetrahydrofuran (THF), dimethylformamide (DMF), dimethyl sulfoxide (DMSO), sulfolane, or combinations thereof. In some embodiments, the first solvent and the second solvent are the same. In other embodiments, the first solvent and the second solvent are different.

In some embodiments of the method described herein, the one or more non-polar solvents and the one or more polar solvents are present in the first solvent or second solvent in a ratio of about 99:1 (v/v), about 98:2 (v/v), about 97:3 (v/v), about 96:4 (v/v), about 95:5 (v/v), about 94:6 (v/v), about 93:7 (v/v), about 92:8 (v/v), about 91:9 (v/v), about 90:10 (v/v), about 85:15 (v/v), about 80:20 (v/v), about 75:25 (v/v), about 70:30 (v/v), about 65:35 (v/v), about 60:40 (v/v), about 55:45 (v/v), or about 50:50 (v/v), or withing a range defined by any two of the aforementioned ratios. For example, in some embodiments, the one or more non-polar solvent and the one or more polar solvent are present in the first solvent or second solvent in a ratio of from about 50:50 (v/v) to about 99:1 (v/v), from about 60:40 (v/v) to about 95:5 (v/v), from about 65:35 (v/v) to about 90:10 (v/v), or from about 70:30 (v/v) to about 85:15 (v/v).

Additional embodiments of the present application relate to an oligonucleotide prepared by any of the methods described herein.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. General Procedure for the Synthesis of Compounds of Formula (I)

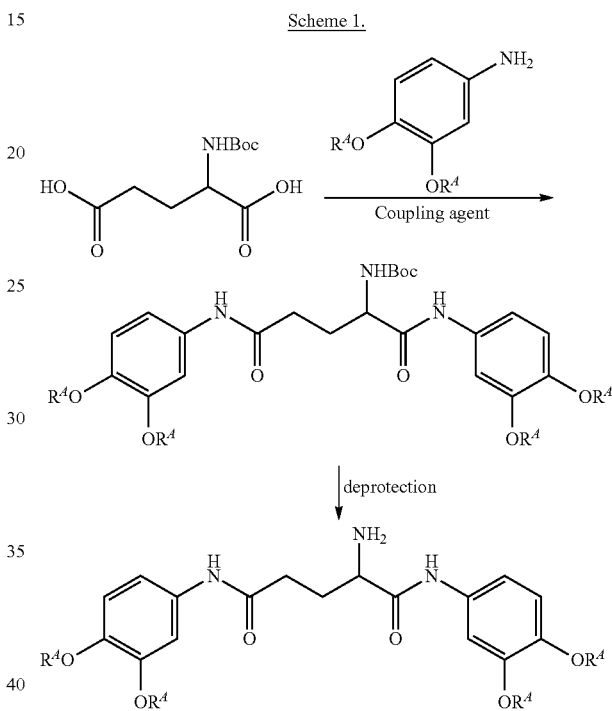

Boc-Glu-OH (Sigma) and an amine compound functionalized with $C_6$-$C_3M$ alkyl groups, O-(Benzotriazol-1-yl)-N,N,N',N'-tetramethyluronium hexafluorophosphate (HBTU), hydroxybenzotriazole (HOBt) and diisopropylethylamine are dissolved in dichloromethane (DCM), and the resulting solution is stirred overnight at room temperature. The mixture is diluted with methanol, concentrated, and filtrated in vacuo. The resulting residue is dried in vacuo give the Boc-protected amide product. Subsequent deprotection with trifluoroacetic acid (TFA) in DCM gives the desired compound of Formula (I). Other compounds disclosed herein may be prepared according to similar methods.

Example 2. Synthesis of Compound

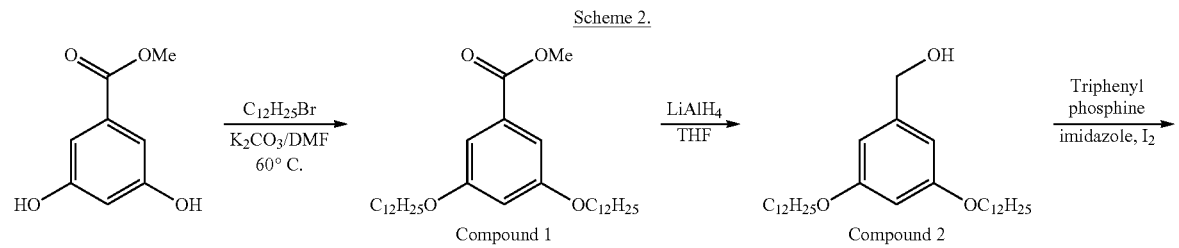

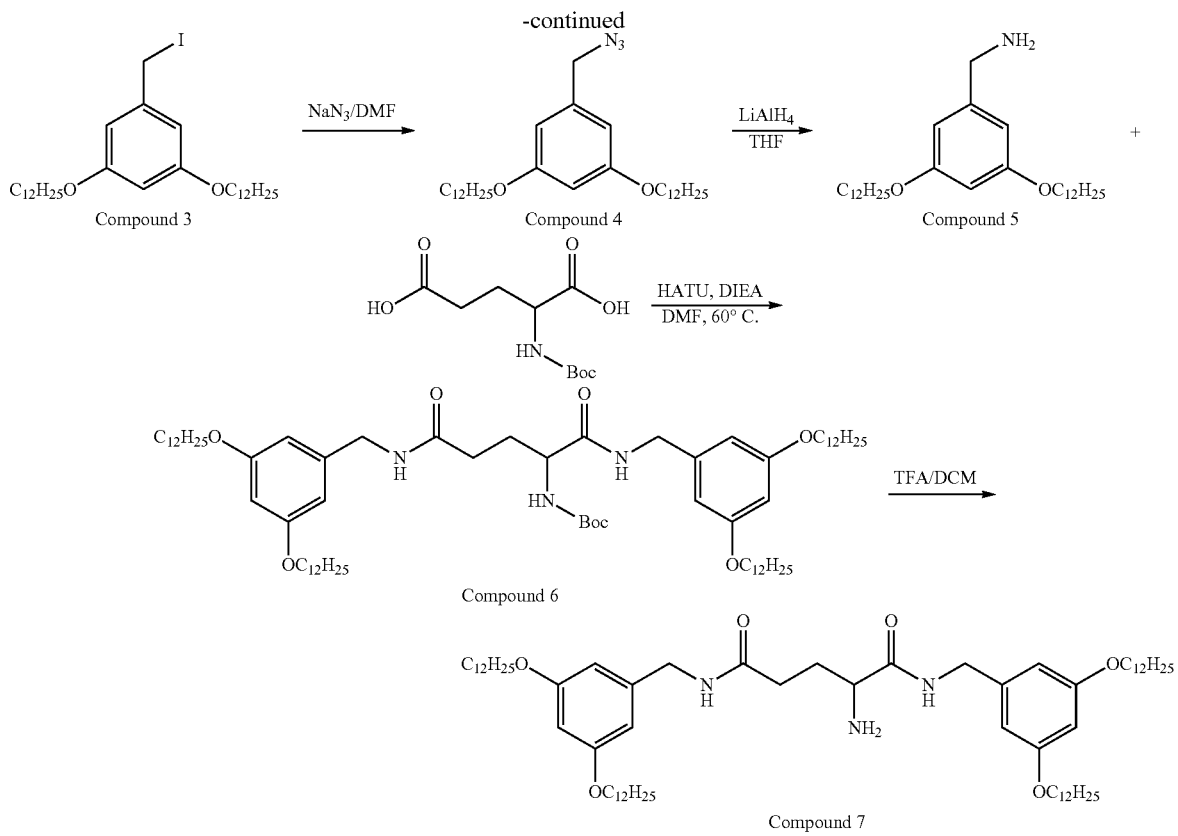

Preparation of Compound 1: Methyl 3,5-dihydroxy benzoate (5.0 g, 29.7 mmol) and $K_2CO_3$ (16.4 g, 118.8 mmol) were dissolved in DMF (300 mL) and stirred for 1 hour before 1-bromododecane (18.5 g, 74.3 mmol) was added. The reaction mixture was stirred at 60° C. for 24 hours. After methyl 3,5-dihydroxy benzoate completely disappeared by thin layer chromatography (TLC), the reaction mixture was poured into 200 mL 1N HCl and 100 g of ice and filtered. The crude product was recrystallized in acetone and $H_2O$ to yield Compound 1 as a white solid (14.6 g, 97%). $^1$H NMR (300 MHz, $CDCl_3$) δ (ppm): 6.40-6.48 (m, 3H), 4.25 (s, 3H), 3.93 (t, J=6.6 Hz, 4H), 1.72-1.81 (m, 4H), 1.40-1.41 (m, 4H), 1.20-1.40 (s, 32H), 0.88 (t, J=6.5 Hz).

Preparation of Compound 2: Compound 1 (5.04 g, 0.01 mol) and $LiAlH_4$ (304 mg, 8 mmol) were added to a 250 mL round bottom flask under Ar gas. Dry THF (80 mL) was added, and the reaction mixture was stirred for 2 hours until Compound 1 was completely consumed. To the reaction mixture was then added 0.3 mL $H_2O$, 0.3 mL of 15% NaOH and 0.9 ml of $H_2O$ and stirred overnight. The reaction mixture was filtered through celite, washed with THF and dried over vacuum to yield Compound 2 as a white solid. (3 g, 63%). $^1$H NMR (300 MHz, $CDCl_3$) δ (ppm): 6.5 (m, 2H), 6.37 (m, 1H), 4.61 (s, 2H), 3.93 (t, 4H, J=7.2 Hz), 1.7-1.82 (m, 4H), 1.4-1.5 (m, 4H), 1.2-1.36 (m, 32H), 0.88 (t, J=6.8 Hz).

Preparation of Compound 3: Compound 2 (2 g, 4.2 mmol) was dissolved in 1,2-dichloroethane (DCE) (40 mL), followed by adding triphenyl phosphine (1.43 g, 5.46 mmol), imidazole (372 mg, 5.46 mmol) and 12 (1.39 g, 5.46 mmol) in portions. The reaction mixture was stirred at room temperature for 1 hour until all of Compound 2 was consumed. The reaction mixture was dried over vacuum, diluted with cold ether, washed with sodium thiosulfate twice and brine once. The organic layer was dried over sodium sulfate and evaporated to dryness. The crude product was purified with hexane:ether 0-50% to yield 2.1 g of Compound 3 as a white solid (85%). $^1$H NMR (300 MHz, $CDCl_3$) δ 6.49 (m, 2H), 6.32 (m, 1H), 4.37 (s, 2H), 3.91 (t, 4H, J=6.45 Hz), 1.7-1.80 (m, 4H), 1.4-1.5 (m, 4H), 1.2-1.4 (m, 32H), 0.88 (t, J=3.6 Hz).

Preparation of Compound 4: Compound 3 (3.5 g, 5.99 mmol) and sodium azide (487 mg, 7.49 mmol) were dissolved in 40 mL DMF and the reaction mixture was stirred at 45° C. for 2 hours. The reaction mixture was cooled to room temperature and 20 mL of water was added. The reaction mixture was stirred on an ice bath for 1 hour until the formation of a white precipitate. The white precipitate was filtered and recrystallized in acetone to yield Compound 4 as a white solid. (2.7 g, 95%). $^1$H NMR (300 MHz, $CDCl_3$) δ 6.41-6.43 (m, 3H), 4.25 (s, 2H), 3.93 (t, 4H, J=6.45 Hz), 1.7-1.80 (m, 4H), 1.4-1.55 (m, 4H), 1.2-1.4 (m, 32H), 0.88 (t, J=6.8 Hz).

Preparation of Compound 5: Compound 4 (4.5 g, 9 mmol) was added to a 200 mL round bottom flask under Ar gas. Dry THF (50 mL) was added to dissolve the compound. $LiAlH_4$ was added slowly while the flask at 0° C. The reaction mixture was stirred at room temperature for 2 hours until the azide compound had been converted to the corresponding amine. Then 0.34 mL of water was added, followed by the addition of 0.34 mL of 15% of NaOH and 1 mL of water. The reaction mixture was stirred at room temperature overnight. The reaction mixture was filtered through celite and washed with THF. The filtrate was concentrated in vacuo and the residue was purified via column chromatography (DCM/methanol 0-5%) to yield Compound 5 (3.84 g, 90%). $^1$H NMR (300 MHz, CDCl$_3$) δ (ppm): 6.45 (m, 2H), 6.34 (m, 1H), 3.93 (t, 4H, J=6.75 Hz), 3.79 (s, 2H), 1.7-1.82 (m, 4H), 1.38-1.48 (m, 4H), 1.22-1.38 (m, 32H), 0.88 (t, 3H, J=6.45 Hz).

Preparation of Compound 6: Compound 5 (3.8 g, 8 mmol), N-Boc glutamic acid (659 mg, 2.67 mmol), and 1-[bis(dimethylamino)methylene]-1H-1,2,3-triazolo[4,5-b]pyridinium 3-oxid hexafluorophosphate (HATU) (2.24 g, 8 mmol) were dissolved in 100 mL DMF followed by the addition of N,N-diisopropylethylamine (DIEA) (1.65 g, 12.8 mmol). The reaction mixture was stirred at 60° C. for 6 hours. The reaction mixture was cooled to room temperature and continued to stir overnight while precipitate was forming. The precipitate was filtered and washed with acetone and water. The crude product was recrystallized in acetone to yield Compound 6 (3.0 g 97%). $^1$H NMR (300 MHz, CDCl$_3$) δ (ppm): 6.35-6.42 (m, 4H), 6.30-6.36 (m, 2H), 4.34 (s, 4H), 4.15 (m, 1H), 3.88 (t, 8H, J=6.75 Hz), 1.2.43 (m, 2H), 1.9-2.2 (m, 2H), 1.67-1.8 (m, 8H), 1.36-1.48 (m, 8H+9H), 1.2-1.38 (m, 64H), 0.88 (t, 12H, J=6.75 Hz).

Preparation of Compound 7: Compound 6 was dissolved in a TFA/DCM solution (5 mL/15 mL), and the reaction was stirred at room temperature overnight. Subsequently, TFA/DCM was removed through co-evaporation with acetonitrile; this process was repeated twice. Following this, acetonitrile was added to the and stirred at room temperature for 1 hour before cooling down in an ice bath. The precipitate was filtered to yield Compound 7 as a white solid (2.25 g, 75%). $^1$H NMR (300 MHz, CDCl$_3$): δ (ppm): 6.35-6.42 (m, 4H), 6.30-6.36 (m, 2H), 4.34 (s, 4H), 4.15 (m, 1H), 3.88 (t, 8H, J=6.75 Hz), 2.51-2.43 (m, 2H), 1.9-2.2 (m, 2H), 1.67-1.8 (m, 8H), 1.36-1.48 (m, 8H+9H), 1.2-1.38 (m, 64H), 0.88 (t, 12H, J=6.75 Hz).

Example 3. General Procedure for the Synthesis of Oligonucleotides

Scheme 3.

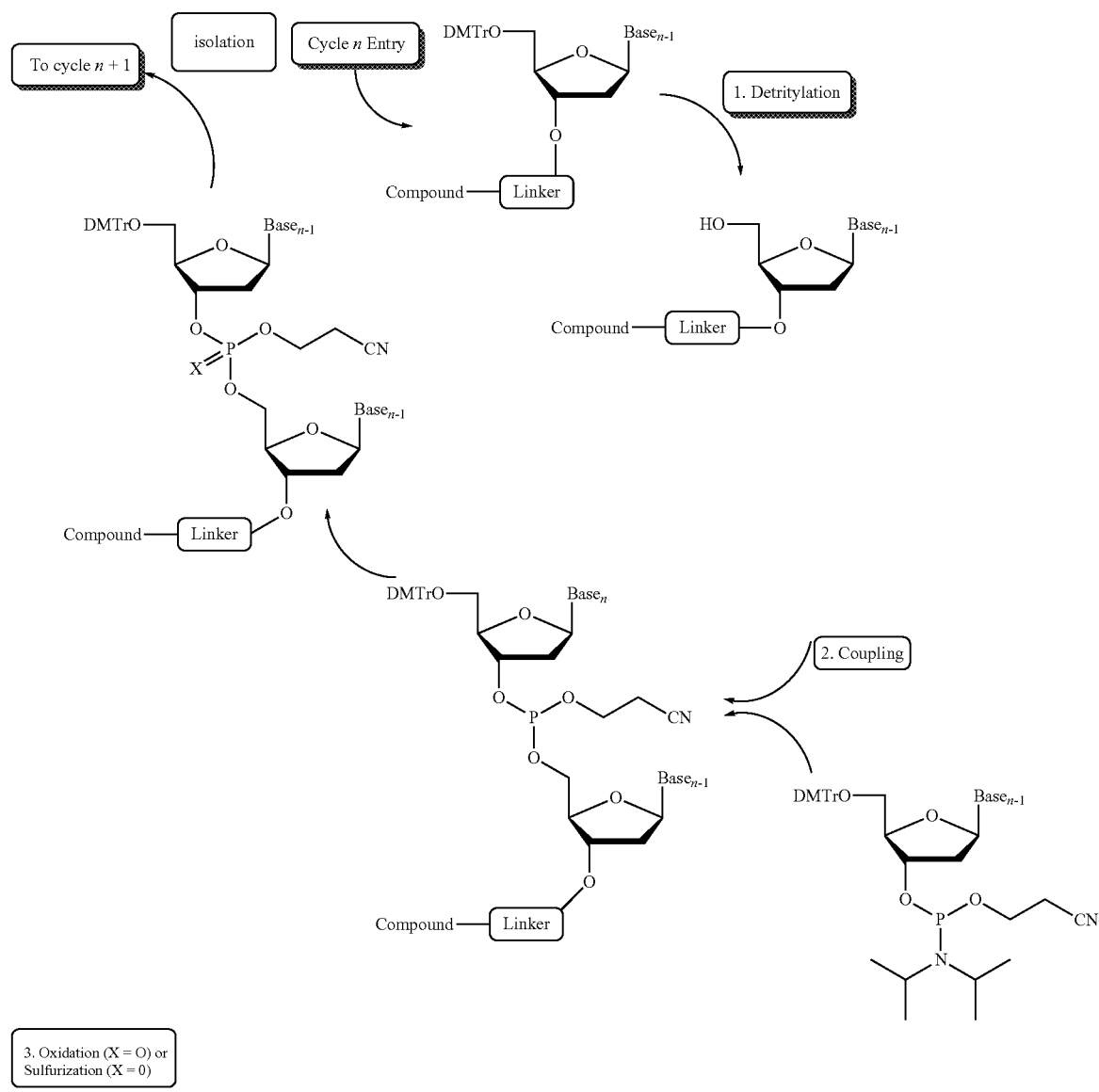

A compound of Formula (I) (1 eq) is dissolved in dichloromethane. Separately, DMTr-dT-3'-succinate TEA salt (Hongene Biotech, 1.12 eq), HBTU (3.37 eq), HOBt (3.37 eq) and diisopropylethylamine (3.37 eq) are dissolved in dry dichloromethane (DCM), and the resulting solution is allowed to stand at room temperature for 15 minutes. The compound of Formula (I) solution and the DMTr-dT-3'-succinate solution are combined and stirred overnight at room temperature. The reaction mixture is then diluted with methanol, concentrated and filtered in vacuo. The resulting residue is dried in vacuo to give the first dT conjugate having a DMTr blocking group at the 5' position. This first 5'-blocked dT conjugate is treated with 5% dichloroacetic acid (DCA)/DCM solution. After stirring for 10 minute, the reaction mixture is precipitated with methanol and concentrated in vacuo. The resulting residue is precipitated with methanol, filtered and rinsed with methanol to give first dT conjugate. To the first conjugate (1 eq) is added benzylthio-1H-tetrazole (HOBt) (2 eq) and DMTr-dT phosphoramidite (Hongene Biotech) (1.5 eq) in dry dichloromethane/acetonitrile (10/1, v/v) at room temperature. After stirring the resulting reaction mixture for 30 min, 2-butanone peroxide/dichloromethane solution is added. After stirring for 10 min, the resulting mixture is precipitated with methanol and concentrated in vacuo to give the 2-dT conjugate bearing a DMTr blocking group. The above-mentioned procedure is repeated as desired to give the oligonucleotide of desired length.

Example 4. Procedure for Preparation of Oligonucleotides Using Small Molecule Anchor Compound 7

Scheme 4.

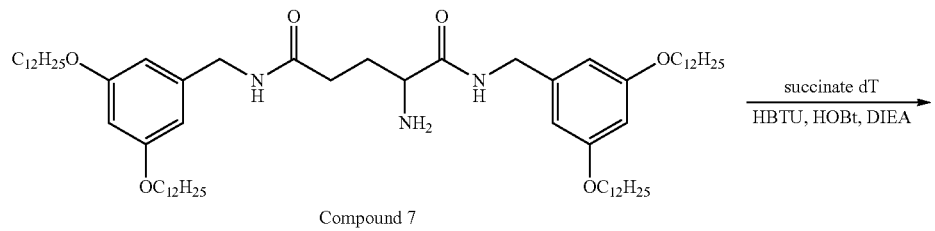

Compound 7

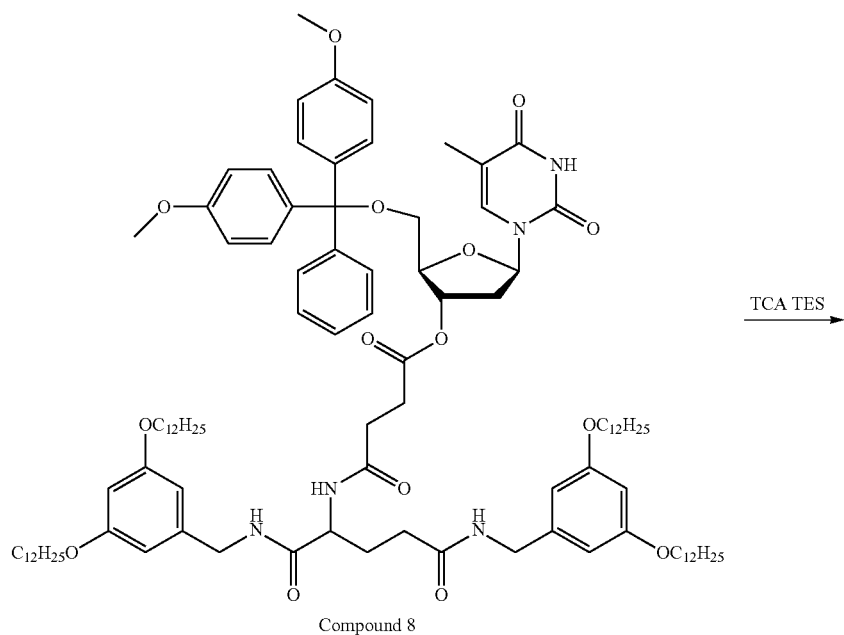

Compound 8

-continued

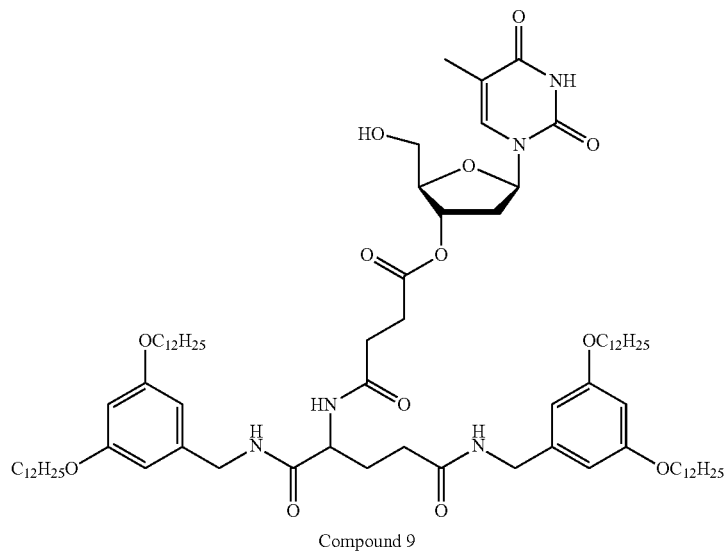
Compound 9

Preparation of Compound 8: To initiate the conjugation of the first thymidine base to the anchor, DMTr-dT-3'-succinate TEA salt (Hongene Biotech), (652 mg, 0.87 mmol) underwent preactivation with HBTU (365 mg, 0.96 mmol), HOBt (130 mg, 0.94 mmol), and DIEA (305 µL, 1.75 mmol) in DCM for 10 minutes. The resulting solution was introduced to Compound 7 (310 mg, 0.29 mmol) and allowed to react for 3 hours. The Ninhydrin test confirmed the completion of the reaction. Subsequently, the product was precipitated using acetonitrile, followed by two acetonitrile washing steps. The structure of the dried intermediate product (433.5 mg, 83%) was confirmed through NMR analysis.

Preparation of Compound 9: The removal of the trityl group from Compound 8 involved the addition of 1.6 mL of a 600 mg/mL trichloroacetic acid (TCA) solution (in DCM, 5.9 mmol) to Compound 8 (396.8 mg, 0.23 mmol). Triethylsilane (TES) (0.560 mL, 3.5 mmol) was introduced as the scavenger reagent, and the reaction proceeded for 10 minutes before acetonitrile precipitation and subsequent washing. The resulting yield was determined to be 91.1%. Elongation of the oligonucleotide is shown in Scheme 5.

Scheme 5.

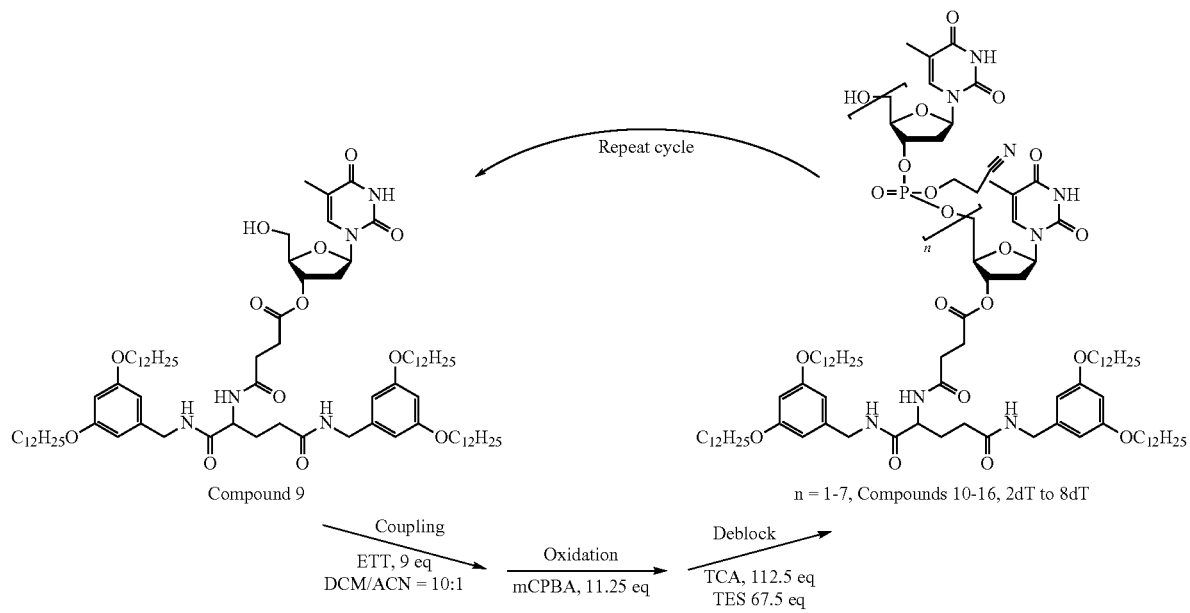

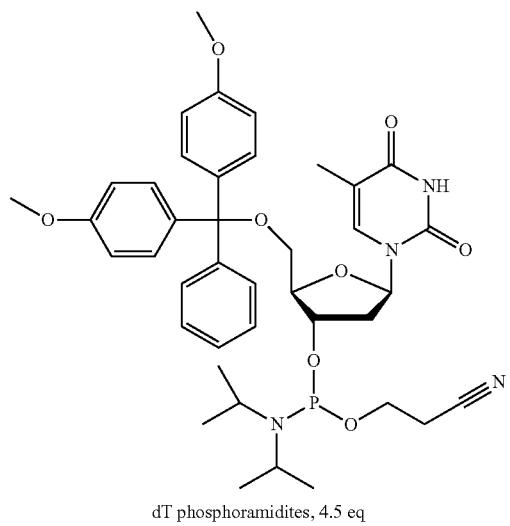

dT phosphoramidites, 4.5 eq

Oligonucleotides comprising 8 dT were synthesized using Compound 9 as the starting material. Compound 9 and DMTr-dT phosphoramidite (Hongene Biotech) (4.5 eq) were left under vacuum overnight to eliminate excess moisture. Subsequently, the 5-(ethylthio)-1H-tetrazole (ETT) solution (0.25 M in acetonitrile, 9 eq.), along with a 10× volume of anhydrous DCM, were injected into the mixture under argon. The reaction proceeded for 3 hours, and a drop was extracted for TLC examination. After confirming the completion of the reaction, meta-chloroperbenzoic acid (mCPBA) (11.25 eq.) was added. After 10 minutes, the excess DCM and acetonitrile were carefully removed using a rotovap. Following the deblock step involving the addition of TCA and TES (112.5 eq and 67.5 eq), the mixture was stirred for an additional 10 minutes before undergoing precipitation with acetonitrile. The final product was subsequently washed with acetonitrile to eliminate impurities before being subjected to lyophilization. After every cycle, a minuscule quantity of the sample was taken for cleavage using AMA solution (1:1 mixture of NH$_4$OH and methylamine). The subsequent product was characterized by HPLC and LC-MS. The process was repeated 7 times.

HPLC results from each cycle revealed a stepwise-right-shifted, sharp, single peak, indicative of high coupling efficiency in every base coupling. The LC-MS result also confirmed the successful synthesis of 8dT oligonucleotide (exact mass: 2370.41). The final product (8dT) demonstrates exceptional purity (91.1%), underscoring the potential of this small molecule as a robust anchor for synthesizing oligonucleotides. The purity of oligonucleotide purity as determined by HPLC is provided below in Table 1.

TABLE 1

Purity of dT oligonucleotides as determined by HPLC

| Oligonucleotide | Purity (%) |
|---|---|
| 2dT | 99.1 |
| 3dT | 97.9 |
| 4dT | 96.7 |
| 5dT | 95.3 |

TABLE 1-continued

Purity of dT oligonucleotides as determined by HPLC

| Oligonucleotide | Purity (%) |
|---|---|
| 6dT | 94.4 |
| 7dT | 93.2 |
| 8dT | 91.1 |

While the present application has been described with reference to the specific embodiments thereof, it should be understood by those skilled in the art that various changes may be made and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A compound for liquid phase oligonucleotide synthesis, having the structure of Formula (IIa), (IIb), (IIc), (IId), (IIe), or (IIf):

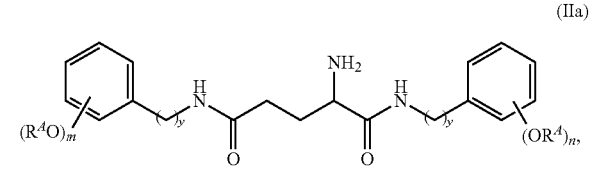

(IIa)

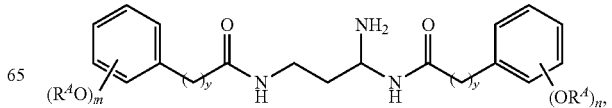

(IIb)

-continued

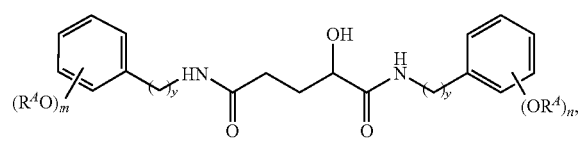
(IIc)

(IId)

(IIe)

(IIf)

wherein each $R^A$ is independently $C_6$-$C_{30}$ alkyl, $C_6$-$C_{30}$ alkenyl, $C_6$-$C_{30}$ alkynyl, 6-30 membered heteroalkylene, —C(=O)($C_6$-$C_{30}$ alkyl), or —C(=O)(6-30 membered heteroalkylene);

y is 0, 1, 2, 3, 4, 5, 6, 7, 8, 9 or 10;

n is 0, 1, 2, or 3; and m is 1, 2, or 3.

2. The compound of claim 1, wherein the compound is a compound of Formula (IIa-1), (IIa-2), (IIa-3), (IIb-1), (IIb-2), (IIc-1), (IIc-2), (IId-1), (IId-2), (IIe-1), (IIe-2), (IIf-1), or (IIf-2):

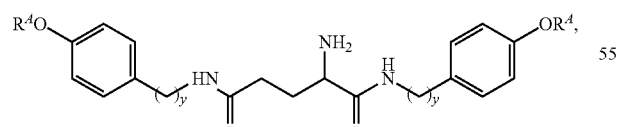
(IIa-1)

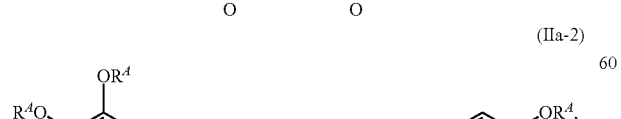
(IIa-2)

-continued

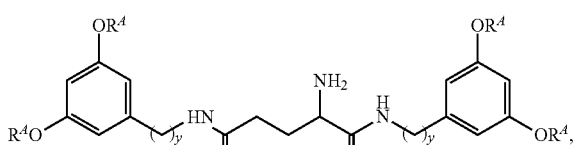
(IIa-3)

(IIb-1)

(IIb-2)

(IIc-1)

(IIc-2)

(IId-1)

(IId-2)

(IIe-1)

-continued

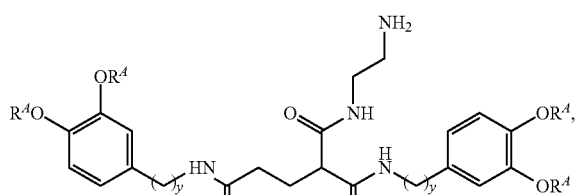
(IIe-2)

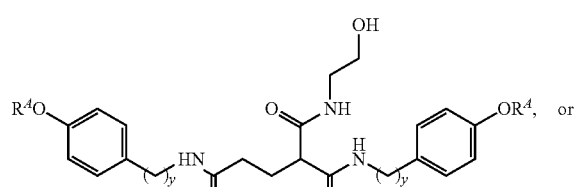
(IIf-1)

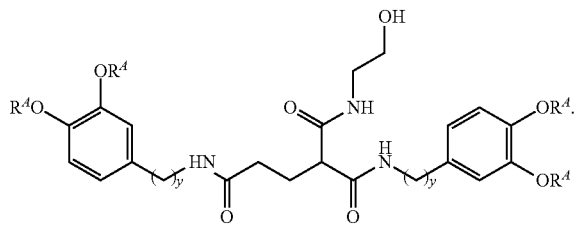
(IIf-2)

3. The compound of claim 1, wherein y is 0 or 1.
4. The compound of claim 1, wherein each $R^A$ is independently $C_6$-$C_{20}$ alkyl or —C(=O)$C_6$-$C_{20}$ alkyl.
5. The compound of claim 4, wherein each $R^A$ is independently ethylhexyl, dodecyl, 3,5,5-trimethylhexyl, 3,7,11 trimethyldodecyl,

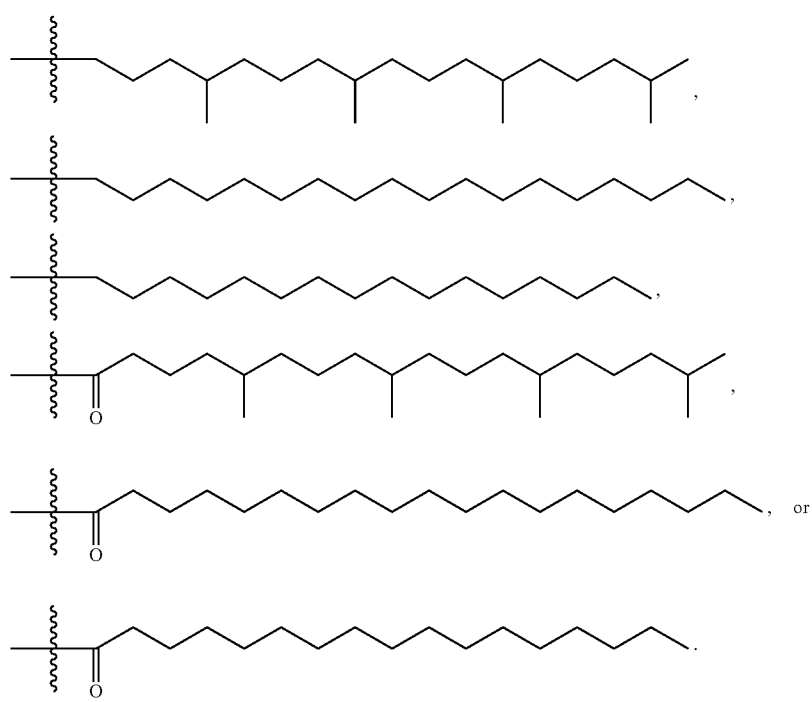

6. The compound of claim 1, wherein the compound is:

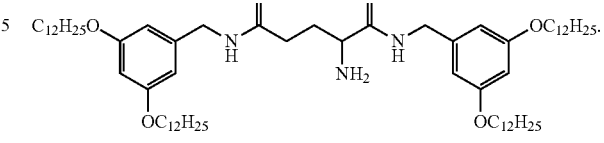

7. A method for preparing an oligonucleotide by liquid phase oligonucleotide synthesis, comprising:
contacting the compound of claim 1 in a first solvent with one or more nucleoside analogs to form a first solvent solution comprising a first bioconjugate having a structure of Formula (IV):

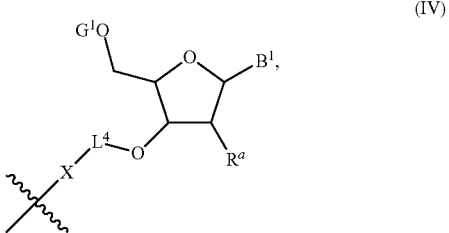
(IV)

wherein
$B^1$ is a nitrogenous base;
$G^1$ is a 5' hydroxy blocking group;
X is O or $NR^{12}$;
$R^{12}$ is H or $C_1$-$C_6$ alkyl;
$R^a$ is —H, —OH, halogen, —O—($C_1$-$C_6$ alkyl), —O—($C_1$-$C_6$ haloalkyl), or —OY, where Y is a 2' hydroxy protecting group; and $L^4$ is a cleavable heteroalkylene linker where one or more carbon atoms is replaced by O, S, N, C(=O) or C(=S).

8. The compound of claim 2, wherein y is 0 or 1.

9. The compound of claim 8, wherein each $R^A$ is independently $C_6$-$C_{20}$ alkyl or —C(=O)$C_6$-$C_{20}$ alkyl.

10. The compound of claim 9, wherein each $R^A$ is independently $C_6$-$C_{20}$ alkyl.

11. The compound of claim 10, wherein each $R^A$ is independently ethylhexyl, dodecyl, 3,5,5-trimethylhexyl, 3,7,11 trimethyldodecyl,

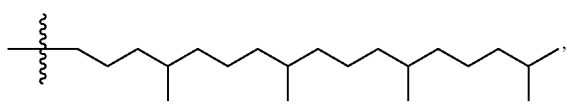

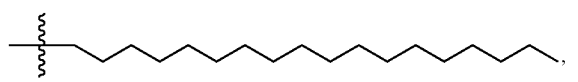

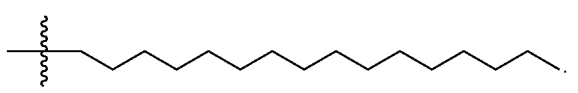

12. The compound of claim 9, wherein each $R^A$ is independently

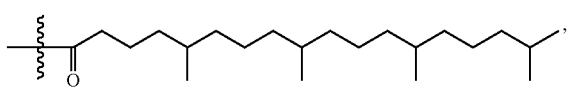

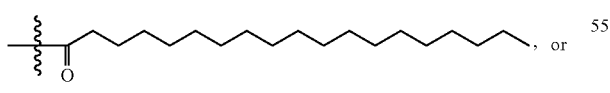

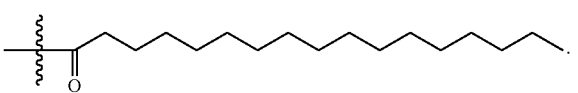

13. The method of claim 7, wherein the structure of Formula (IV) is also represented by Formula (IVa):

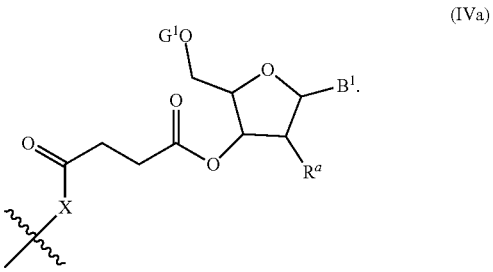

(IVa)

14. The method of claim 7, wherein $B^1$ is independently optionally protected adenine, optionally protected deaza adenine, optionally protected cytosine, optionally protected guanine, optionally protected deaza guanine, optionally protected thymine or optionally protected uracil.

15. The method of claim 7, wherein $G^1$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

16. The method of claim 7, further comprising removing the 5' hydroxy blocking group ($G^1$) to form a 5' unblocked first bioconjugate.

17. The method of claim 16, further comprising washing the 5' unblocked first bioconjugate with an aqueous solvent to remove impurities from the 5' unblocked first bioconjugate.

18. The method of claim 16, further comprising isolating the 5' unblocked first bioconjugate.

19. The method of claim 16, further comprising:

(a) reacting the 5' unblocked first bioconjugate with one or more nucleoside phosphoramidite analogs in a second solvent to form a second bioconjugate comprising the structure of Formula (V):

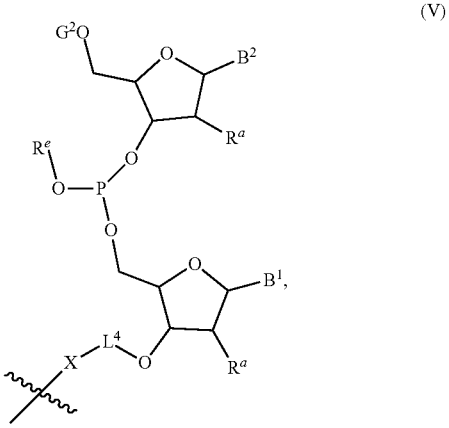

(V)

wherein
G² is a 5' hydroxy blocking group;
B² is a nitrogenous base; and
Rᵉ is a phosphite protecting group;
(b) oxidizing the phosphite moiety in Formula (V);
(c) removing the 5' blocking group G² to form a 5' unblocked second bioconjugate comprising the structure of Formula (V'):

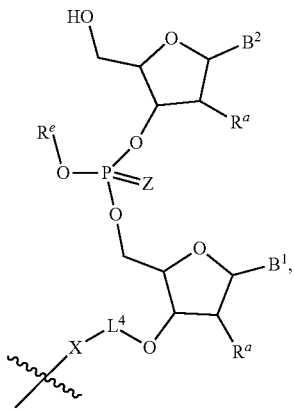

(V')

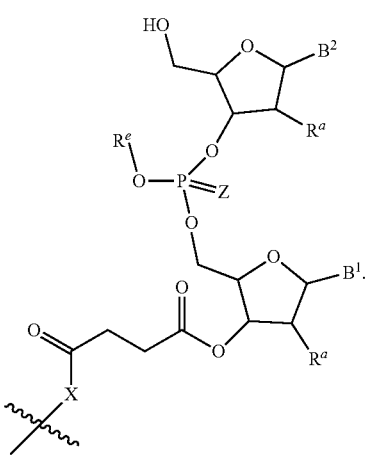

(V'a)

wherein
Z is O or S; and
(d) isolating or purifying the 5' unblocked second bioconjugate.

20. The method of claim 19, wherein the structure of Formula (V) is also represented by (Va) and the Formula (V') is also represented by Formula (V'a):

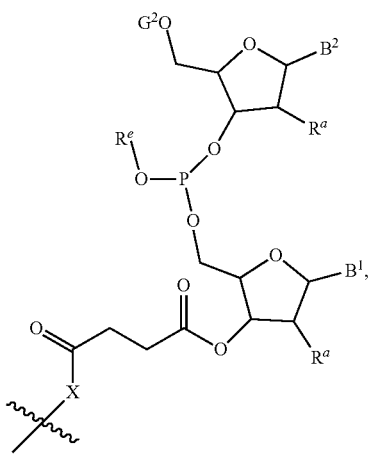

(Va)

21. The method of claim 19, wherein B² is independently optionally protected adenine, optionally protected deaza adenine, optionally protected cytosine, optionally protected guanine, optionally protected deaza guanine, optionally protected thymine, or optionally protected uracil.

22. The method of claim 19, wherein G² is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

23. The method of claim 19, wherein steps (a)-(d) are repeated multiple cycles until one or more desired length of oligonucleotides have been synthesized.

24. The method of claim 23, wherein steps (a)-(d) are repeated at least 10 cycles.

25. The method of claim 23, further comprising removing the oligonucleotides from the compound.

26. The method of claim 19, wherein the first or the second solvent comprises one or more non-polar solvents or one or more polar solvents, or combinations thereof.

* * * * *